(12) United States Patent
Roy et al.

(10) Patent No.: US 11,806,137 B2
(45) Date of Patent: Nov. 7, 2023

(54) REAL-TIME MEAL DETECTION BASED ON SENSOR GLUCOSE AND ESTIMATED PLASMA INSULIN LEVELS

(71) Applicant: MEDTRONIC MINIMED, INC., Northridge, CA (US)

(72) Inventors: Anirban Roy, Agoura Hills, CA (US); Benyamin Grosman, Winnetka, CA (US); Neha J. Parikh, West Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 0 days.

(21) Appl. No.: 18/314,791

(22) Filed: May 9, 2023

(65) Prior Publication Data

US 2023/0277097 A1 Sep. 7, 2023

Related U.S. Application Data

(63) Continuation of application No. 18/060,268, filed on Nov. 30, 2022.
(Continued)

(51) Int. Cl.
*A61B 5/145* (2006.01)
*A61M 5/172* (2006.01)
(Continued)

(52) U.S. Cl.
CPC ...... *A61B 5/14532* (2013.01); *A61B 5/14865* (2013.01); *A61B 5/7475* (2013.01);
(Continued)

(58) Field of Classification Search
None
See application file for complete search history.

(56) References Cited

U.S. PATENT DOCUMENTS

| 3,560,082 | A1 | 10/2013 | Wei |
| 9,398,869 | B2 | 7/2016 | Kovatchev et al. |

(Continued)

FOREIGN PATENT DOCUMENTS

| EP | 2400882 B1 | 5/2017 |
| WO | 2020230123 A1 | 11/2020 |

OTHER PUBLICATIONS

Boughton, C.K. et al., "Fully Automated Closed-loop Glucose Control Compared With Standard Insulin Therapy in Adults With Type 2 Diabetes Requiring Dialysis: an Open-label, Randomized Crossover Trial," Nature Medicine, Aug. 2021, vol. 27, No. 8, pp. 1471-1476.

(Continued)

*Primary Examiner* — Manuel A Mendez
(74) *Attorney, Agent, or Firm* — Weaver Austin Villeneuve & Sampson LLP

(57) ABSTRACT

Disclosed herein are techniques related to automatic real-time meal detection. In some embodiments, the techniques involve obtaining a plurality of glucose concentration values and a plurality of plasma insulin concentration estimations, each glucose concentration value corresponding with a respective plasma insulin concentration estimation; generating an output based on applying a meal detection model to the plurality of glucose concentration values and the plurality of plasma insulin concentration estimations; and determining, based on the output, that a glucose concentration value of the plurality of glucose concentration values corresponds to an ongoing glycemic response to a meal.

20 Claims, 9 Drawing Sheets

Related U.S. Application Data

(60) Provisional application No. 63/285,042, filed on Dec. 1, 2021.

(51) Int. Cl.
*G16H 20/17* (2018.01)
*A61B 5/00* (2006.01)
*G16H 40/63* (2018.01)
*A61B 5/1486* (2006.01)
*A61M 5/142* (2006.01)

(52) U.S. Cl.
CPC .......... *A61M 5/1723* (2013.01); *G16H 20/17* (2018.01); *G16H 40/63* (2018.01); *A61M 2005/14208* (2013.01)

(56) References Cited

U.S. PATENT DOCUMENTS

| | | | |
|---|---|---|---|
| 9,827,371 B2 * | 11/2017 | Soru | A61M 5/1723 |
| 9,867,937 B2 | 1/2018 | Saint et al. | |
| 10,357,606 B2 | 7/2019 | Rosinko et al. | |
| 10,610,154 B2 | 4/2020 | Kovatchev et al. | |
| 10,792,423 B2 * | 10/2020 | Chen | A61M 5/1723 |
| 11,024,429 B2 | 6/2021 | Patek et al. | |
| 11,430,557 B2 | 8/2022 | Mougiakakou et al. | |
| 2010/0298685 A1 * | 11/2010 | Hayter | A61B 5/14532 |
| | | | 604/500 |
| 2012/0059673 A1 * | 3/2012 | Cohen | G16H 20/10 |
| | | | 705/3 |
| 2014/0066889 A1 | 3/2014 | Grosman et al. | |
| 2016/0354543 A1 | 12/2016 | Cinar et al. | |
| 2017/0185748 A1 * | 6/2017 | Budiman | G16H 50/20 |
| 2018/0174675 A1 | 6/2018 | Roy et al. | |
| 2019/0374137 A1 | 12/2019 | Kovatchev et al. | |
| 2020/0101221 A1 | 4/2020 | Lintereur et al. | |
| 2020/0197605 A1 | 6/2020 | Haidar | |
| 2020/0214629 A1 | 7/2020 | Kovatchev et al. | |
| 2021/0001038 A1 | 1/2021 | Rosinko | |
| 2021/0050085 A1 | 2/2021 | Hayter et al. | |
| 2021/0077719 A1 | 3/2021 | Cardinali et al. | |
| 2021/0093782 A1 | 4/2021 | Saint et al. | |
| 2021/0093783 A1 | 4/2021 | Lintereur et al. | |
| 2021/0154405 A1 * | 5/2021 | Kearns | G16H 40/63 |
| 2021/0186417 A1 | 6/2021 | Braig et al. | |
| 2021/0205534 A1 | 7/2021 | Jepson et al. | |
| 2021/0244880 A1 | 8/2021 | Lee et al. | |
| 2021/0259590 A1 * | 8/2021 | Metzmaker | G16H 40/67 |
| 2021/0361864 A1 | 11/2021 | Lintereur et al. | |
| 2022/0062548 A1 | 3/2022 | Zheng et al. | |
| 2022/0062553 A1 | 3/2022 | Constantin et al. | |
| 2022/0168505 A1 * | 6/2022 | Li | A61M 5/1723 |
| 2022/0233773 A1 | 7/2022 | Rueda et al. | |
| 2022/0241500 A1 * | 8/2022 | Jiang | G16H 50/20 |
| 2022/0257859 A1 | 8/2022 | Grosman et al. | |
| 2022/0323676 A1 * | 10/2022 | Krey | G16H 20/17 |

OTHER PUBLICATIONS

Boughton, C.K., et al., Fully Closed-loop Insulin Delivery—Are We Nearly There Yet?, The Lancet. Digital health, Nov. 2021, vol. 3, No. 11, pp. e689-e690.

Boughton, C.K., et al., "Fully Closed-loop Insulin Delivery in Inpatients Receiving Nutritional Support: a Two-centre, Open-label, Randomised Controlled Trial," The lancet. Diabetes Endocrinology, May 2019, vol. 7, No. 5, pp. 368-377.

Cinar A., et al., "Incorporating Unannounced Meals and Exercise in Adaptive Learning of Personalized Models for Multivariable Artificial Pancreas Systems," Journal of Diabetes Science and Technology, Jul. 2018, vol. 12(5), pp. 953-966.

For Clinicians "A General Introduction and guide to AndroidAPS", 8 pages.

Forlenza, G. P., et al., "Fully Closed-Loop Multiple Model Probabilistic Predictive Controller Artificial Pancreas Performance in Adolescents and Adults in a Supervised Hotel Setting," Diabetes Technology Therapeutics, May 2018, vol. 20, No. 5, pp. 335-343.

Garcia-Tirado, J. et al., "Advanced Closed-Loop Control System Improves Postprandial Glycemic Control Compared With a Hybrid Closed-Loop System Following Unannounced Meal," Diabetes Care, 2021, vol. 44, No. 10, pp. 2379-2387.

International Search Report and Written Opinion dated Mar. 31, 2023 in PCT Application No. PCT/US2022/080777.

Invitation to Pay Additional Fees and, Where Applicable, Protest Fee dated Mar. 29, 2023 in PCT Application No. PCT/US2022/051586.

"Diabetes Technology Meeting 2021 Day #3 Highlights—Draft", Closer Look, Nov. 3-6, 2021, pp. 1-14.

Loutseiko, M. et al., "Closed-Loop Insulin Delivery Utilizing Pole Placement to Compensate for Delays in Subcutaneous Insulin Delivery," Journal of Diabetes Science and Technology, Nov. 2011, vol. 5, No. 6, pp. 1342-1351.

McDermid, E., "AI May Facilitate Fully Closed-loop Insulin Delivery," Medicine Matters Diabetes, May 6, 2021, 3 Pages.

Sherr, J.L et al., "Automated Insulin Delivery: Benefits, Challenges and Recommendations. A Consensus Report of the Joint Diabetes Technology Working Group of the European Association for the Study of Diabetes and the American Diabetes Association," Diabetologia, Jan. 2023, vol. 66, No. 1, pp. 3-22.

Templer, S., "Closed-Loop Insulin Delivery Systems: Past, Present, and Future Directions," Frontiers in Endocrinology, Jun. 2022, vol. 13, No. 919942, 9 Pages.

* cited by examiner

REAL-TIME MEAL DETECTION BASED ON SENSOR GLUCOSE AND ESTIMATED PLASMA INSULIN LEVELS

CROSS-REFERENCE TO RELATED APPLICATIONS

This application is a continuation of and claims the benefit of U.S. patent application Ser. No. 18/060,268, filed Nov. 30, 2022, entitled "REAL-TIME MEAL DETECTION BASED ON SENSOR GLUCOSE AND ESTIMATED PLASMA INSULIN LEVELS," which claims the benefit of U.S. Provisional Application No. 63/285,042, filed Dec. 1, 2021, entitled "REAL-TIME MEAL DETECTION BASED ON SENSOR GLUCOSE AND ESTIMATED PLASMA INSULIN LEVELS," each of which is incorporated herein by reference in its entirety.

TECHNICAL FIELD

The present disclosure relates generally to real-time meal detection based on physiological indicia.

BACKGROUND

A person (e.g., a patient or a user of a diabetes management device) may use insulin therapy to manage type I or type II diabetes. Insulin therapy may include use of insulin infusion systems for delivering or dispensing insulin. An insulin infusion system may include an infusion device which typically includes a small motor and drive train components configured to deliver insulin from a reservoir into the body of a person, e.g., via a percutaneous needle or a cannula placed in the subcutaneous tissue. Insulin infusion systems may facilitate management of diabetes.

SUMMARY

Disclosed herein are techniques related to real-time detection of a meal. The techniques may be practiced in a variety of ways, such as using a processor-implemented method; a system comprising one or more processors and one or more processor-readable media; and/or one or more processor-readable media (e.g., non-transitory processor-readable media).

In one aspect of the present disclosure, a system for automatic real-time meal detection is disclosed. In some embodiments, the system may include: one or more processors; and one or more processor-readable media storing instructions which, when executed by the one or more processors, cause performance of one or more operations including: obtaining a plurality of glucose concentration values and a plurality of plasma insulin concentration estimations, each glucose concentration value of the plurality of glucose concentration values corresponding with a respective plasma insulin concentration estimation of the plurality of plasma insulin concentration estimations; generating an output based on applying a meal detection model to the plurality of glucose concentration values and the plurality of plasma insulin concentration estimations; and determining, based on the output, that a glucose concentration value of the plurality of glucose concentration values corresponds to an ongoing glycemic response to a meal.

In another aspect of the present disclosure, a processor-implemented method is disclosed. In some embodiments, the processor-implemented method includes: obtaining a plurality of glucose concentration values and a plurality of plasma insulin concentration estimations, each glucose concentration value corresponding with a respective plasma insulin concentration estimation; generating an output based on applying a meal detection model to the plurality of glucose concentration values and the plurality of plasma insulin concentration estimations; and determining, based on the output, that a glucose concentration value of the plurality of glucose concentration values corresponds to an ongoing glycemic response to a meal.

In another aspect of the present disclosure, one or more processor-readable media storing instructions are disclosed. In some embodiments, when executed by one or more processors, the instructions cause performance of: obtaining a plurality of glucose concentration values and a plurality of plasma insulin concentration estimations, each glucose concentration value corresponding with a respective plasma insulin concentration estimation; generating an output based on applying a meal detection model to the plurality of glucose concentration values and the plurality of plasma insulin concentration estimations; and determining, based on the output, that a glucose concentration value of the plurality of glucose concentration values corresponds to an ongoing glycemic response to a meal.

BRIEF DESCRIPTION OF THE DRAWINGS

The above and other aspects and features of the disclosure will become more apparent in view of the following detailed description when taken in conjunction with the accompanying drawings wherein like reference numerals identify like elements.

DETAILED DESCRIPTION

Figure 1:
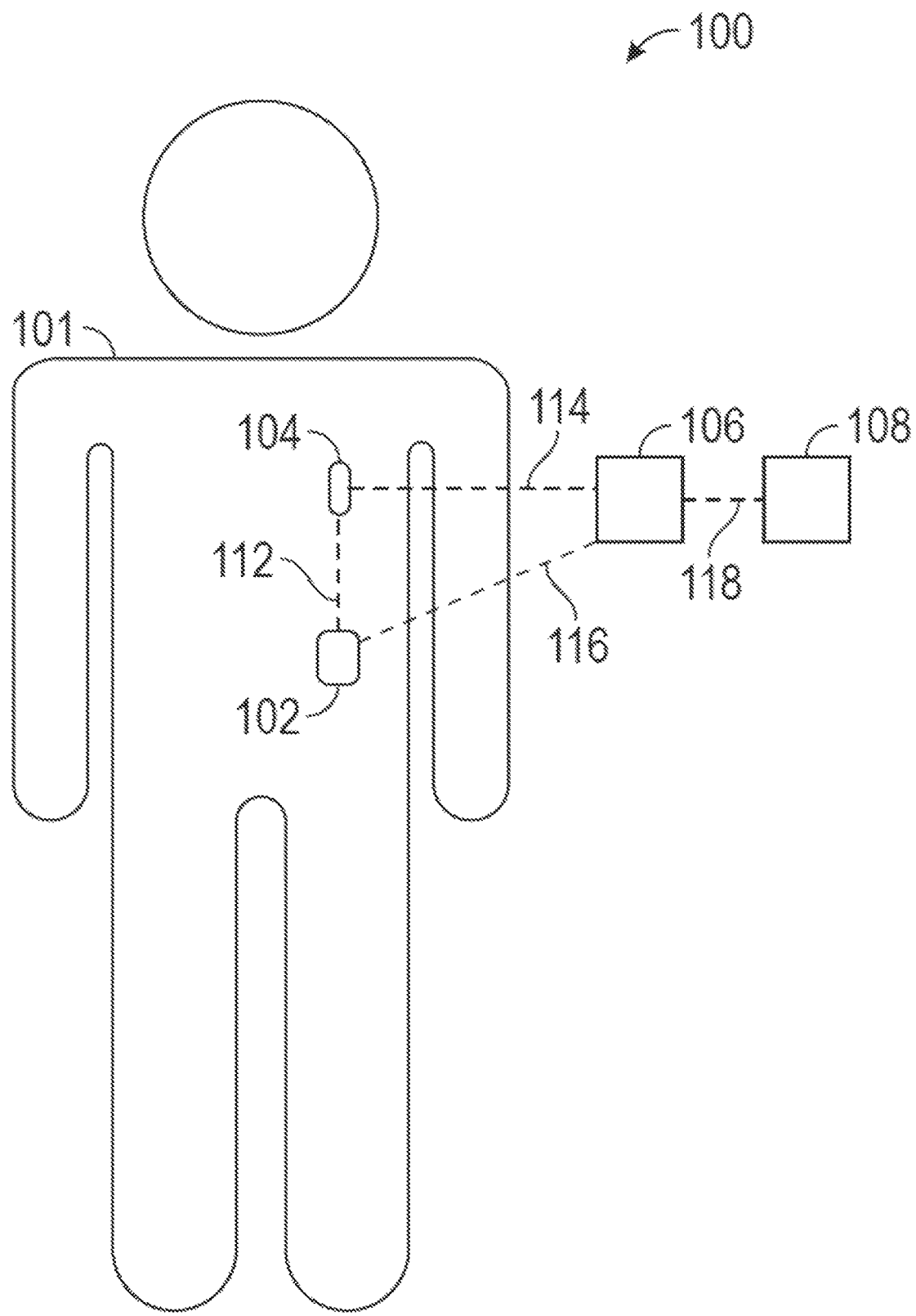
FIG. 1 is a diagram of an example of a therapy delivery system, in accordance with aspects of the present disclosure.

Therapeutic substances (e.g., insulin) may be delivered to a diabetic patient to manage, for example, type I or type II diabetes. Delivering appropriate amounts of a therapeutic substance at appropriate times can help maintain glucose levels within a target range (e.g., a euglycemic range) in the body to prevent hyperglycemia or hypoglycemia conditions.

For example, consumption of a meal by diabetic patients may cause their glucose levels to rise during a postprandial state, especially for meals containing carbohydrates (e.g., starches, sugars, fibers). A postprandial state, stage, or period includes a time period following the start of a meal during which meal consumption may cause a glycemic response (e.g., a glucose level increase) in the patient's body. Postprandial periods typically exhibit a relatively rapid rise in glucose levels, and if sufficient insulin is not delivered early in the postprandial period at the latest, postprandial hyperglycemia can result. However, prompt and sufficient insulin delivery is difficult without prompt and accurate meal detection.

Meal detection can be performed in a variety of ways. For example, the occurrence of a meal may be automatically determined based on detecting a rise in glucose levels. However, this approach is susceptible to error stemming from glucose level increases that are not attributable to meals (e.g., sensor artifacts or certain types of exercise).

According to certain embodiments disclosed herein, one or more techniques for meal detection can be used to automatically and accurately detect the occurrence of a meal in real time using a plurality of physiological indicia. For example, blood glucose concentration estimates and plasma insulin concentration estimates may be used to detect an ongoing glycemic response to the meal. By using plasma insulin concentration estimates in addition to blood glucose concentration estimates, false positives (e.g., due to sensor artifacts) can be reduced or eliminated, thereby increasing detection accuracy. In some embodiments, detection accuracy can be further increased by analyzing blood glucose and plasma insulin concentration estimates within a predetermined time window (e.g., three hours) corresponding to a typical (e.g., average) length of time between consecutive meals. Employing such a time window provides contextual information that can increase confidence when determining whether or not a set of blood glucose and plasma insulin concentration estimates corresponds to an ongoing glycemic response to a meal.

Furthermore, early, accurate, and automatic meal detection enables insulin delivery close to the onset of an ongoing glycemic response to a meal, thereby mitigating the risk of postprandial hyperglycemia. For instance, early, accurate, and automatic meal detection can afford ample time to notify a patient or a caretaker who can then take appropriate action (e.g., manually inject insulin via a syringe or a pen-shaped insulin delivery device). Alternatively, insulin can be delivered in a more automated fashion, such as by using a closed-loop control system to automatically deliver correction boluses (e.g., correction micro-boluses) to counteract a meal. This can be achieved based on temporarily increasing the size of correction boluses, for example, by temporarily lowering a target glucose value for correction boluses and/or temporarily decreasing an insulin sensitivity factor (ISF). There are many advantages in using a plurality of correction boluses that collectively constitute at least part of a meal bolus (e.g., an amount of insulin delivered to at least partially counteract a glycemic response to a meal). One advantage is the ability to quickly mitigate the risk of insulin delivered in error (e.g., in response to a meal detection that was incorrect) by preventing further delivery of correction boluses and temporarily suspending basal dosages. Another advantage is that the amounts of correction boluses can be dynamically determined as glucose concentration values are obtained, thereby avoiding reliance on carb counting or some other error-prone approach for estimating meal content. Yet another advantage is that in conjunction with automated meal detection, automated delivery of correction boluses enables a fully automated insulin delivery system (e.g., an artificial pancreas).

The present disclosure is described primarily with respect to insulin delivery systems. Aspects and embodiments of the present disclosure can be practiced with one or more types of insulin (e.g., fast-acting insulin, intermediate-acting insulin, and/or slow-acting insulin). For example, fast-acting insulin may be used for both basal dosages and bolus dosages.

Although the present disclosure is described primarily with respect to insulin delivery systems, the scope of the present disclosure is not limited to insulin delivery systems. Rather, the present disclosure applies to and can be implemented for other therapy systems as well. For example, some techniques of the present disclosure may be adapted for practice in relation to glucagon delivery systems (e.g., instead of applying a model trained to detect meals, applying a model trained using similar physiological indicia to detect decreasing glucose levels that will violate a hypoglycemic threshold without glucagon intervention).

Discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other non-transitory information storage media that may store instructions to perform operations and/or processes by, e.g., one or more processor or processor apparatus (e.g., system on a chip) or a device associated with such processor(s).

In the context of this disclosure, a "module" may refer to a set of computer-executable instructions and/or a hardware processor configured to execute a set of computer-executable instructions. A hardware processor may be an integrated circuit device associated with a computing device, such as a server or a user device (e.g., a desktop computer, a laptop computer, a tablet computer, a mobile phone, or the like), which is programmable to perform specific tasks. In some embodiments, multiple modules may be implemented as a single module. In some embodiments, a single module may be implemented as multiple modules. In some embodiments, two or more modules may be executable by the same device (e.g., the same computing device or delivery device).

Unless explicitly stated, the methods described herein are not constrained to a particular order or sequence. Additionally, some of the described methods or elements thereof can occur or be performed simultaneously or concurrently.

FIG. 1 depicts an example therapy delivery system 100 for a person 101. System 100 may be an insulin delivery system. The depicted therapy delivery system 100 includes a delivery device 102, a monitoring device 104, a computing device 106, and an optional remote or cloud computing system 108. The delivery device 102, the monitoring device 104, and the computing device 106 may be embodied in various ways, including being disposed in one or more device housings. For example, in some embodiments, all of the devices 102-106 may be disposed in a single device housing. In some embodiments, each of the devices 102-106 may be disposed in a separate device housing. In some embodiments, two or more of the devices 102-106 may be disposed in the same device housing, and/or a single device 102, 104, or 106 may have two or more parts that are disposed in two or more housings. Such embodiments, and combinations thereof, are contemplated to be within the scope of the present disclosure.

FIG. 1 also depicts communications links 112-118. The communications links 112-118 may each be a wired connection and/or a wireless connection. In the case where two devices are located in the same device housing, the communication link may include, for example, wires, cables, and/or communication buses on a printed circuit board, among other things. In the case where two devices are separated from each other in different device housings, the communication links may be wired and/or wireless connections. Wired connections may include, without limitation, an Ethernet connection, a USB connection, and/or another type of physical connection. Wireless connections may include, without limitation, a cellular connection, a Wi-Fi connection, a Bluetooth® connection, a mesh network connection, and/or another type of connection using a wireless communication protocol. Some embodiments of the communication links 112-118 may use direct connections, such as Bluetooth® connections, and/or may use connections that route through one or more networks or network devices (not shown), such as an Ethernet network, a Wi-Fi network, a cellular network, a satellite network, an intranet, an extranet, the Internet, and/or the Internet backbone, among other types of networks. Various combinations of wired and/or wireless connections may be used for the communication links 112-118.

Aspects of the insulin delivery system 100 are described below. Further aspects and details may be described in U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893. The entire contents of each of the foregoing United States Patents are hereby incorporated by reference herein.

The delivery device 102 is configured to deliver a therapeutic substance (e.g., insulin) to a person 101. The delivery device 102 may be secured to the person 101 (e.g., to the body or clothing of the person 101) or may be implanted on or in the body of the person 101. In some embodiments, the delivery device 102 may include a reservoir, an actuator, a delivery mechanism, and a cannula (not shown). The reservoir may be configured to store an amount of the therapeutic substance. In some embodiments, the reservoir may be refillable or replaceable. The actuator may be configured to drive the delivery mechanism. In some examples, the actuator may include a motor, such as an electric motor. The delivery mechanism may be configured to move the therapeutic substance from the reservoir through the cannula. In some examples, the delivery mechanism may include a pump and/or a plunger. The cannula may facilitate a fluidic connection between the reservoir and the body of the person 101. The cannula and/or a needle may facilitate delivery of the therapeutic substance to a tissue layer, vein, or body cavity of the person 101. During operation, the actuator, in response to a signal (e.g., a command signal), may drive the delivery mechanism, thereby causing the therapeutic substance to move from the reservoir, through the cannula, and into the body of the person 101.

The components of the delivery device 102 described above are merely provided as examples. The delivery device 102 may include other components, such as, without limitation, a power supply, a communication transceiver, computing resources, and/or user interfaces, among other things. Persons skilled in the art will recognize various implementations of the delivery device 102 and the components of such implementations. All such implementations and components are contemplated to be within the scope of the present disclosure.

With continuing reference to FIG. 1, the monitoring device 104 is configured to detect a physiological condition (e.g., a glucose concentration level) of the person 101 and may also be configured to detect other things. The monitoring device 104 may be secured to the body of the person 101 (e.g., to the skin of person 101 via an adhesive) and/or may be at least partially implanted into the body of the person 101. Depending on the particular location or configuration, the monitoring device 104 may be in contact with biological matter (e.g., interstitial fluid and/or blood) of the person 101.

The monitoring device 104 includes one or more sensors (not shown), such as, without limitation, electrochemical sensors, electrical sensors, and/or optical sensors. As persons skilled in the art will understand, an electrochemical sensor may be configured to respond to the interaction or binding of a biological marker to a substrate by generating an electrical signal based on a potential, conductance, and/or impedance of the substrate. The substrate may include a material selected to interact with a particular biomarker, such as glucose. The potential, conductance, and/or impedance may be proportional to a concentration of the particular biomarker. In the case of electrical sensors, and as persons skilled in the art will understand, an electrical sensor may be configured to respond to an electrical biosignal by generating an electrical signal based on an amplitude, frequency, and/or phase of the electrical biosignal. The electrical biosignal may include a change in electric current produced by the sum of an electrical potential difference across a tissue, such as the nervous system, of the person 101. In some embodiments, the electrical biosignal may include portions of a potential change produced by the heart of the person 101 over time, e.g., recorded as an electrocardiogram, that are indicative of a glucose level of the person 101. In the case of optical sensors, as persons skilled in the art will understand, an optical sensor may be configured to respond to the interaction or binding of a biological marker to a substrate by generating an electrical signal based on change in luminance of the substrate. For example, the substrate may include a material selected to fluoresce in response to contact with a selected biomarker, such as glucose. The fluorescence may be proportional to a concentration of the selected biomarker.

In some embodiments, the monitoring device 104 may include other types of sensors that may be worn, carried, or coupled to the person 101 to measure activity of the person 101 that may influence the glucose levels or glycemic response of the person 101. As an example, the sensors may include an acceleration sensor configured to detect an acceleration of the person 101 or a portion of the person 101, such as the person's hands or feet. The acceleration (or lack thereof) may be indicative of exercise, sleep, or food/beverage consumption activity of the person 101, which may influence the glycemic response of the person 101. In some embodiments, the sensors may include heart rate and/or body temperature, which may indicate an amount of physical exertion experienced by the person 101. In some embodiments, the sensors may include a GPS receiver which detects GPS signals to determine a location of the person 101.

The sensors described above are merely provided as examples. Other sensors or types of sensors for monitoring physiological condition, activity, and/or location, among other things, will be recognized by persons skilled in the art and are contemplated to be within the scope of the present disclosure. For any sensor, the signal provided by a sensor shall be referred to as a "sensor signal."

The monitoring device 104 may include components and/or circuitry configured to pre-process sensor signals. Pre-processing may include, without limitation, amplification, filtering, attenuation, scaling, isolation, normalization, transformation, sampling, and/or analog-to-digital conversion, among other things. Persons skilled in the art will recognize various implementations for such pre-processing, including, without limitation, implementations using processors, controllers, ASICS, integrated circuits, hardware, firmware, programmable logic devices, and/or machine-executable instructions, among others. The types of pre-processing and their implementations are merely provided as examples. Other types of pre-processing and implementations are contemplated to be within the scope of the present disclosure. In some embodiments, the monitoring device 104 may not perform pre-processing.

As used herein, the term "sensed data" shall mean and include the information represented by a sensor signal or by a pre-processed sensor signal. In some embodiments, sensed data may include glucose levels in a person 101, acceleration of a part of the person 101, heart rate of the person 101, temperature of the person 101, and/or geolocation (e.g., GPS location) of the person 101, among other things. The monitoring device 104 may communicate sensed data to the delivery device 102 via communication link 112 and/or to the computing device 106 via communication link 114. Use of sensed data by the delivery device 102 and/or by the computing device 106 will be described later herein.

The computing device 106 provides processing capabilities and may be implemented in various ways. In some embodiments, the computing device 106 may be a consumer device, such as a smartphone, a computerized wearable device (e.g., a smartwatch), a tablet computer, a laptop computer, or a desktop computer, among others, or may be a special purpose device (e.g., a portable control device) provided by, for example, the manufacturer of the delivery device 102. In some embodiments, the computing device 106 may be "processing circuitry" (defined below) that is integrated with another device, such as the delivery device 102. In some embodiments, the computing device 106 may be secured to the person 101 (e.g., to the body or clothing of person 101), may be at least partially implanted into the body of person 101, and/or may be held by the person 101.

For each of the embodiments of the computing device 106, the computing device 106 may include various types of logic circuitry, including, but not limited to, microprocessors, microcontrollers, digital signal processors (DSPs), application specific integrated circuits (ASICs), field-programmable gate arrays (FPGAs), central processing units (CPU), graphics processing units (GPU), programmable logic devices, memory (e.g., random access memory, volatile memory, non-volatile memory, etc.), or other discrete or integrated logic circuitry, as well as combinations of such components. The term "processing circuitry" may generally refer to any of the foregoing logic circuitry, alone or in combination with other logic circuitry, or any other circuitry for performing computations.

Aspects of the delivery device 102, the monitoring device 104, and the computing device 106 have been described above. One or more of the devices 102-106 may include a user interface (not shown) that presents information to the person 101 and/or receives information from the person 101. The user interface may include a graphical user interface (GUI), a display device, a keyboard, a touchscreen, a speaker, a microphone, a vibration motor, buttons, switches, and/or other types of user interfaces. Persons skilled in the art will recognize various types of user interfaces that may be used, and all such user interfaces are contemplated to be within the scope of the present disclosure. For example, where the computing device 106 is a consumer device such as a smart phone, tablet computer, laptop computer, or the like, the user interfaces would include a display device, a physical and/or virtual keyboard, and/or audio speakers provided by such consumer devices, among other things. In some embodiments, a user interface may notify the person 101 of sensed data (e.g., glucose level) and/or insulin delivery data (e.g., rates of historic, current, or future insulin delivery) and may present alerts to the person 101. In some embodiments, a user interface may receive inputs from the person 101, which may include, for example, a requested change in insulin delivery and/or a meal indication, among other things. The descriptions and embodiments above regarding user interfaces are merely provided as examples, and other types and other uses of user interfaces are contemplated to be within the scope of the present disclosure.

The following describes communications between the devices 102-106 and cooperation between the devices 102-106 with respect to insulin delivery. As depicted in FIG. 1, and as mentioned above, the devices 102-106 may communicate with each other via communication links 112-116. In some embodiments, the computing device 106 may control operation of the delivery device 102 and/or the monitoring device 104. For example, the computing device 106 may generate one or more signals (e.g., a command signal) that cause the delivery device 102 to deliver insulin to the person 101, e.g., as a basal dosage and/or a bolus dosage. In some embodiments, the computing device 106 may receive data associated with insulin delivery (e.g., insulin delivery data) from the delivery device 102 and/or receive sensed data (e.g., glucose levels) from the monitoring device 104 and may perform computations based on the insulin delivery data, the sensed data, and/or other data to control the delivery device 102. Insulin delivery data may include, but is not limited to, a type of insulin being delivered, historical insulin delivery rates and/or amounts, current insulin delivery rate and/or amount, and/or user input affecting insulin delivery. As persons skilled in the art will understand, in a closed-loop operating mode, computing device 106 may communicate dosage commands to the delivery device 102 based on a difference between a current glucose level in the body of the person 101 (e.g., received from the monitoring device 104) and a target glucose level (e.g., determined by the computing device 106). The dosage commands may indicate an amount of insulin to be delivered and/or a rate of insulin delivery and may regulate the current glucose level toward the target glucose level. Examples of closed-loop operations for insulin infusion systems are described in U.S. Pat. Nos. 6,088,608, 6,119,028, 6,589,229, 6,740,072, 6,827,702, 7,323,142, and 7,402,153, and in United States Patent Application Publication Nos.: 2014/0066887 and 2014/0066889. The entire contents of each of the foregoing patents and publications are hereby incorporated by reference herein.

With continuing reference to FIG. 1, the remote or cloud computing system 108 may be a proprietary remote/cloud computing system or a commercial cloud computing system including one or more server computing devices. The remote/cloud computing system 108 may provide additional computing resources on-demand as needed when the computing resources of a client computing device (e.g., the computing device 106) are not sufficient. The computing device 106 and the remote/cloud computing system 108 may communicate with each other through a communication link 118, which may traverse one or more communication networks (not shown). The communication networks may include, without limitation, an Ethernet network, Wi-Fi network, a cellular network, a satellite network, an intranet, an extranet, the Internet, and/or the Internet backbone, among other types of networks. Persons skilled in the art will recognize implementations for the remote/cloud computing system 108 and how to interface with such systems through various types of networks. For example, the remote/cloud computing system 108 may include an array of processing circuitry (defined above) and may execute machine-readable instructions. Such implementations, interfaces, and networks are contemplated to be within the scope of the present disclosure.

An example therapy delivery system has been described above. For convenience, the description below may primarily refer to an insulin delivery system as an example of the therapy delivery system. However, it is intended that any aspect, embodiment, or description relating to an insulin delivery system shall be applicable to a therapy delivery system which delivers a therapy other than insulin.

As described above, meal consumption by diabetic patients may cause their glucose levels to rise during postprandial periods, especially for meals containing carbohydrates. But some meals may not be announced by patients, and thus information about the meals may not be available for determining appropriate insulin dosages and/or for delivering appropriate insulin dosages. Thus, it may be desirable to automatically detect meal intake (without the need for user input) as early as possible (e.g., within minutes of the start of a meal) such that insulin can be delivered to a patient to prevent postprandial hyperglycemia. However, there are accuracy concerns with many approaches for automatic meal detection. A meal can be automatically detected, for example, by a gesture sensor, but some gestures (e.g., cigarette smoking, nose picking, or nail biting) may be mistaken for meal consumption gestures (e.g., gestures related to raising and lowering a cup or utensil). Additionally or alternatively, a meal can be automatically detected based solely on changes in glucose levels, but relying only on glucose concentration values (e.g., measurements or estimates) as inputs can often result in incorrect meal detections (e.g., due to sensor artifacts or other non-meal events that can result in glucose level increases).

According to certain embodiments disclosed herein, automatic meal detection can be performed using both glucose concentration values and plasma insulin concentration estimations as inputs to detect an ongoing glycemic response to a meal in real time. Automatic real-time meal detection may be performed using a machine learning model to generate one or more output values based on one or more input variables. In some cases, usage of plasma insulin concentration estimations as inputs in conjunction with the glucose concentration values as disclosed herein may improve overall accuracy of the automatic meal detection (e.g., from 91% to 96% accuracy). A machine learning model may be trained before it is used to make an inference from new input data. Training a machine learning model may involve, for example, determining parameters of the machine learning model, such as values of weights associated with one or more nodes of a neural network model. In some embodiments, a machine learning model may be trained in a supervised manner using a training data set that includes labeled training data. The labeled training data may include inputs and corresponding annotated outputs that the machine learning model is to approximate using learned weight values. In some other embodiments, a machine learning model may be trained in an unsupervised manner in which parameters of the machine learning model may be determined without using labeled training data.

In some implementations, the parameter(s) of a machine learning model may be trained via loss minimization by feeding a training dataset to the machine learning model. For example, training a machine learning model may include optimization of parameters (e.g., weights or biases) of the machine learning model using techniques such as gradient descent and backpropagation techniques. A validation dataset may also be allocated (e.g., about 20%) from the training dataset to validate a trained machine learning model before deploying the machine learning model.

As used herein, a "classifier" may refer to a type of machine learning model that is trained to categorize inputs into one or more classes of a set of classes. For instance, classes of a classifier for meal detection may be labeled as "glycemic response to a meal" or "not a glycemic response to a meal." Inputting data into a trained classifier may result in an output that categorizes the input data into a meal or not a meal. Thus, a properly trained classifier may provide an estimation of a mapping between input variables and discrete (as opposed to continuous) output variables. A classifier may be trained, for example, through a supervised fashion (including optimization and backpropagation), where the training data may comprise known and labeled information.

In some cases, the trained classifier may use a regression technique such as logistic regression, which uses a logistic function to model a variable (such as a weighted sum of glucose concentration values and plasma insulin concentration (Ip) estimations) that may have multiple possible discrete outcomes, e.g., a binary or dichotomous outcome such as "glycemic response to a meal" or "not a glycemic response to a meal." Logistic regression can map the predicted values to probabilities using, for example, a sigmoid function. A sigmoid function can map values between one end to another (e.g., 0 to 1), where one end may correspond to a meal and the other end may correspond to not a meal. In some implementations, one or more threshold values may be needed for the classifier to map the input data to one of the discrete outcomes. For example, if the probability is determined to be above a 0.2 threshold needed to be classified as a "0" but below a 0.8 threshold needed to be classified as a "1," then the machine learning model may consider the determination invalid or null rather than one of the binary outcomes.

In some cases, the trained classifier may use a neural network such as a long short-term memory (LSTM) network, which is a type of recurrent neural network (RNN) capable of learning context and order. A RNN may perform the same task (looping back) for each successive element of a sequence, e.g., time series data, and the output may depend on the previous calculation. Each element may be associated with a corresponding layer of the RNN. The RNN may store an internal state, akin to a memory, which is determined based on the previously performed task at a previous time step and the current input at a current time step. Unlike a typical RNN, a LSTM may pass additional information (sometimes known as "cell memory") from one time step to another, which helps capture long-term dependencies through multiple layers, carrying information between points in time and passing new information between states, which is more difficult to do with typical RNNs. That is, LSTMs can better remember previous information and use it for processing the current input. LSTMs can also discard irrelevant information. The output may be based on a sigmoid function (e.g., SoftMax), making LSTMs applicable to binary determinations such as "glycemic response to a meal" or "not a glycemic response to a meal."

Figure 2:
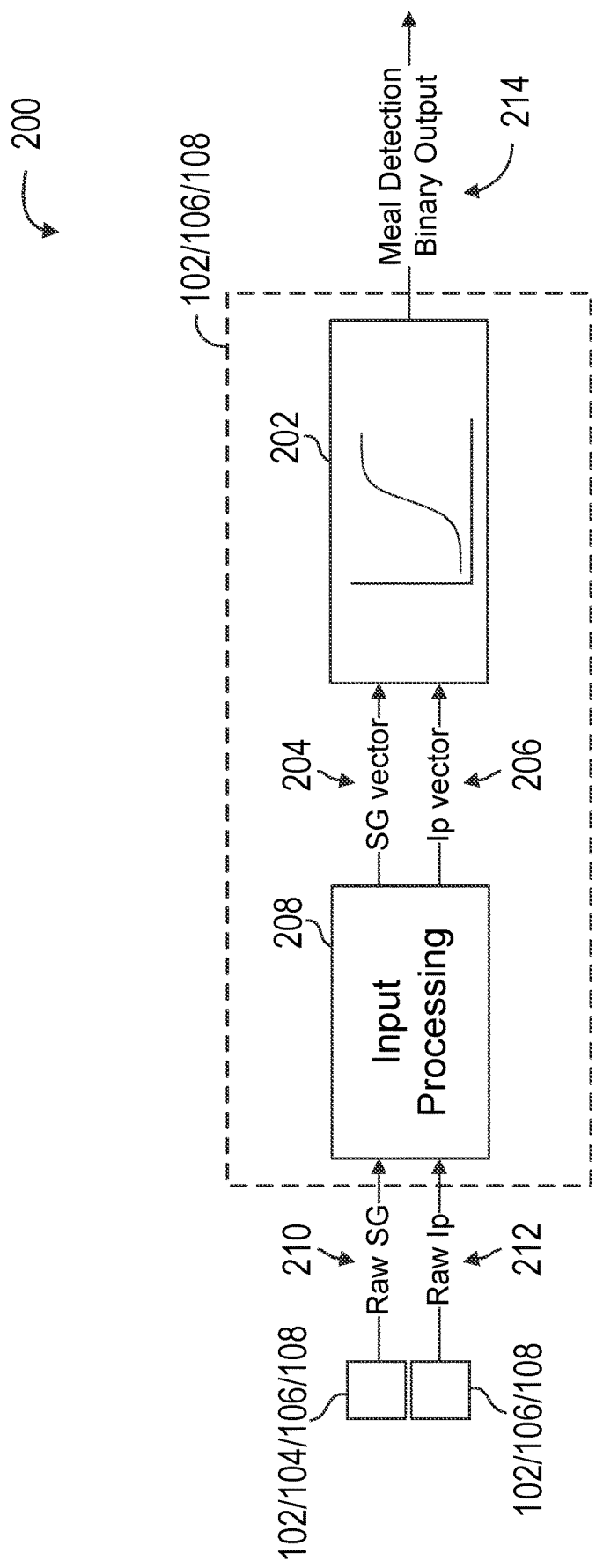
FIG. 2 is a block diagram illustrating an example of a system including a machine learning model trained to detect a meal, according to some embodiments.

FIG. 2 is a block diagram illustrating an example of a system 200 using a machine learning model 202 to detect a meal, according to some embodiments. Machine learning model 202 may be applied to input data that includes past and present physiological indicia of a meal. Values of the physiological indicia may be calculated or collected over a period of time that is at least as long as a typical inter-meal fasting period. Applying trained parameters to the physiological indicia enables determining a probability that a meal (e.g., carbohydrate intake) has recently taken place or is ongoing. Based on the probability, machine learning model 202 can be used to make a binary determination (yes/no) as to whether a meal has taken place.

System 200 may include all or part of system 100. As will be described in greater detail below, in some embodiments of the system 200, sensor glucose (SG) concentration data 210 may be obtained from a delivery device 102, a monitoring device 104, a computing device 106, and/or a computing system 108 (e.g., the monitoring device 104 may obtain interstitial glucose concentration measurements that are converted into SG data 210 by the delivery device 102, the monitoring device 104, the computing device 106, or the computing system 108); and plasma insulin concentration (Ip) data 212 may be estimated by a delivery device 102, a computing device 106, and/or a computing system 108 (e.g., the delivery device 102 may track insulin delivery data that is converted into Ip data 212 by the delivery device 102, the computing device 106, or the computing system 108). Raw data including SG concentration data 210 and estimated Ip data 212 may be processed by an input processing module 208, which may be configured to, among other things, place SG values and Ip values into first input vector 204 and second input vector 206, respectively. Vectors 204, 206 may each have a particular length for storing values of physiological indicia (e.g., a length sufficient to store values calculated or collected over a three-hour time period). These input vectors 204, 206 may be provided as input to the machine learning model 202. In some embodiments, application of the machine learning model 202 may be performed by the delivery device 102. In some embodiments, application of the machine learning model 202 may be performed by the computing device 106. In some embodiments, application of the machine learning model 202 may be performed by the remote or cloud computing system 108.

In some embodiments, the machine learning model 202 may be trained (e.g., according to an approach described above) and configured to determine, based on a classification approach as described above, whether a patient has recently begun consuming a meal (which usually involves carbohydrate intake). In some cases, a machine learning model may be population-trained, where the training dataset may be obtained from a group of patients, e.g., data obtained from studies involving type-I diabetic subjects. In some cases, a machine learning model may be alternatively or additionally trained for a specific patient using a training dataset obtained from the specific patient. The training dataset may include sensor glucose (SG) values and estimated plasma insulin concentration (Ip) values at regular intervals (e.g., every five minutes) over a fixed period of time (e.g., trailing three hours), and may also include labeled data (e.g., known postprandial stages, times of meal or carbohydrate intake).

In some embodiments, SG concentration data 210 may be obtained via a delivery device, a monitoring device, a computing device, and/or a remote/cloud computing system (e.g., delivery device 102, monitoring device 104, computing device 106, and/or computing system 108). The monitoring device (e.g., CGM) may be configured to substantially continuously (e.g., every 5 min) measure signals indicative of interstitial glucose levels using an interstitial glucose sensor. Blood glucose levels can be estimated (e.g., by the delivery device, the monitoring device, the computing device, or the remote/cloud computing system) based on the measured signals indicative of the interstitial glucose levels. More specifically, while a sensor of the monitoring device may not be inserted directly into a blood vessel or require blood samples (e.g., drawn from a finger prick) to measure blood glucose (BG) levels directly, the sensor may be inserted into subcutaneous tissue to measure electrical signals indicative of the glucose level in the interstitial fluid. Based on the electrical signals indicative of the interstitial glucose levels, blood glucose levels can be indirectly estimated (e.g., by converting the interstitial glucose measurements into blood glucose estimates based on a calibration process). These estimated blood glucose measurements may sometimes be referred to as sensor glucose (SG) data/values herein and may be used as the sensor glucose concentration data 210. Although SG values may not exactly match BG measurements taken directly from blood, SG can be a highly representative and accurate estimation of BG.

In some embodiments, plasma insulin concentration (Ip) data 212 may be estimated using a pharmacodynamic model of how quickly insulin delivered subcutaneously is absorbed into the bloodstream. For example, the pharmacodynamic model may include two differential equations: one representing subcutaneous insulin concentration $I_{sc}$ and one representing plasma insulin concentration $I_p$, as shown in Eqns. 1 and 2:

$$I_{sc}'(t) = -k_d * I_{sc}(t) + k_d * J(t); \qquad \text{Eqn. 1}$$

$$I_p'(t) = -k_{cl} * I_{sc}(t) - k_{cl} * I_p(t); \qquad \text{Eqn. 2}$$

In Eqn. 1, $k_d$ is the subcutaneous insulin absorption factor, and J represents the amount of subcutaneous insulin delivery. Hence, Eqn. 1 models the rate of appearance of insulin in subcutaneous tissue. In Eqn. 2, $k_{cl}$ represents a plasma insulin absorption factor. Hence, Eqn. 2 models the rate of appearance of insulin in the bloodstream. Therefore, the concentration of plasma insulin may be modeled and estimated using Eqns. 1 and 2, based on the subcutaneous delivery of insulin.

In some embodiments, $k_d$ and $k_{cl}$ may be universal constants (e.g., population-based constants as opposed to patient-specific constants). In such embodiments, $I_p$ may be normalized (e.g., modified for a specific patient) as part of the estimation (or as part of input processing as described below), e.g., based on a median insulin total daily dose. For example, $I_p$ may be normalized by dividing with 50% of a six-day median insulin total daily dose (TDD). In some embodiments, such estimations may be performed by the delivery device 102, as it has information on how much insulin is exogenously delivered to the patient. In some embodiments, such estimations may be performed by another device, such as the computing device 106 or the computing system 108 (e.g., by obtaining from the delivery device 102 how much insulin is delivered to the patient).

In some embodiments, SG data 210 and estimated Ip data 212 may be processed by an input processing module 208 of the delivery device 102, the computing device 106, or the computing system 108. The processing module 208 may receive input data (e.g., a continually received stream of SG and/or Ip data 210, 212), normalize some of the input data (e.g., Ip data 212), fill gaps (e.g., corresponding to missing SG values or SG values that were invalidated due to being deemed unreliable) in some of the input data (e.g., by using an adjacent SG value or via interpolation based on adjacent SG values), match SG and Ip values that correspond in time (e.g., having the same timestamp or corresponding to the same time period), create data structures (e.g., vectors or matrices) for storing SG and Ip values, identify SG and Ip values to place into data structures (e.g., vectors 204, 206), and/or store SG and Ip values in data structures.

In some embodiments, the input to the machine learning model 202 may include a plurality of glucose concentration values (e.g., SG values in a first input vector 204) and a plurality of plasma insulin concentration estimations (e.g., Ip values in a second input vector 206). In some implementations, the SG values in the first input vector 204 and the Ip values in the second input vector 206 may correspond (e.g., in time), where each glucose concentration value may have a corresponding plasma insulin concentration estimation (e.g., at about the same timestamp and/or at the same relative positions within vectors 204 and 206). As an example, a first glucose concentration value may correspond to a measurement obtained at about 11:00, and a first plasma insulin concentration estimation may correspond to the estimated plasma insulin concentration at about 11:00. A subsequent, second glucose concentration value may correspond to a measurement obtained at about 11:05, and a subsequent, second plasma insulin concentration estimation may correspond to the estimated plasma insulin concentration at about 11:05. Thus, each glucose concentration value in vector 204 may form a time-corresponding pair with a respective plasma insulin concentration estimation in vector 206.

As noted above, SG values and Ip values provided to the machine learning model 202 may be contained in respective data structures, e.g., a first input vector 204 containing a set of discrete SG values, and a second input vector 206 containing a set of discrete Ip values. As noted above, using both SG and Ip as inputs to the machine learning model 202 may improve the accuracy of the output. The data structures may be formed via input processing module 208, which may place raw data and/or other information into data structures, such as vectors. The raw data may include sensor glucose concentration data 210 (which may have been pre-processed by, e.g., normalizing or conditioning signals obtained from the monitoring device) and plasma insulin concentration estimation data 212 obtained using the insulin absorption model.

In certain implementations, glucose concentration values and plasma insulin concentration estimations processed by input processing module 208 may be placed in a single data structure rather than separate structures. For example, a 2×N matrix may comprise respective rows (or columns) for SG and Ip.

In some implementations, each data point within the data structures may be a SG or Ip value for a predetermined time interval, e.g., a five-minute interval. For example, sensor glucose concentration data 210 may be obtained and plasma insulin concentration data 212 may be estimated (e.g., using the insulin absorption model) continuously or more frequently than every five minutes (e.g., every minute), and input processing module 208 may determine representative values for each five-minute interval by, e.g., selecting one out of every five values or calculating the mean, median, or mode of every five values. This may remove anomalies or noise and result in a higher likelihood of having valid data points and/or a more accurate representation of changes over time. As stated above, the glucose values and insulin estimations may be corresponding in time, e.g., pairs having about the same timestamp.

However, in some implementations, SG values and Ip values may not correspond in time, but rather may be within a predetermined time range of each other. For example, SG values may be offset (e.g., regularly offset) from the Ip values by some amount of time (e.g., a few seconds), up to a maximum of the interval (e.g., five minutes). In some implementations, SG and Ip values in the first input vector 204 and the second input vector 206, respectively, may be provided with different frequency, e.g., every five minutes for SG and every minute for Ip. This may allow some flexibility in how quickly glucose values are obtained and insulin estimations are estimated, provide more granularity for some physiological indicia (e.g., Ip), and/or allow each value or estimation to be provided as soon as available. However, in these implementations, a timing relationship may still exist between the SG values and Ip values within the input vectors 204, 206 (e.g., each SG value corresponds to the same time window as five Ip values).

In some implementations, the number of SG and Ip data points to be provided to the machine learning model 202 (e.g., via first and second input vectors 204, 206) may be determined based on the length of the time window, the length of the intervals between consecutive data points, and/or the total number of data points to be provided to or that are specified for the machine learning model 202. For example, 36 values may be provided for each of SG and Ip, creating a three-hour moving window of values obtained at regular intervals of five-minutes. Each set of 36 values may represent the 36 most recent samples of SG and the 36 most recent estimates of Ip.

In some scenarios, data points may be provided as a data stream such that subsequent windows of values can be identified based on shifting the time window forward in time by one data point. For example, when a new pair of data points is obtained, a new pair of input vectors can be formed to include the new pair of data points along with the immediately preceding 35 pairs of data points.

The moving window of time may be sized to include a typical inter-meal fasting period. Stated differently, the moving window of time may be sized to include a fasting period and to exclude a period of postprandial glucose level increase prior to the fasting period. Time windows sized in this manner may provide contextual information that can reduce meal detection time. For example, if a time window includes a past SG value corresponding to a previously detected meal, then it is less likely that the current SG value corresponds to a meal; and if a time window does not include a past SG value corresponding to a previously detected meal, then it is more likely that the current SG value corresponds to a meal.

Although the moving window of time is described herein using the example of a three-hour time period, it should be appreciated that different lengths for the moving window of time are also contemplated by this disclosure. Various quantities of data points sampled, sampling rates, and length of vectors other than those provided above may be used to determine window size. As but one illustrative example, the most recent 60 samples of SG and Ip may be provided over a one-hour moving window with a sampling rate of one sample per minute. In some implementations, the moving window may be greater than 30 minutes and up to three hours, or longer. In some implementations, the size of a moving window of time may be fixed or variable (e.g., periodically adjusted by calculating an average inter-meal time period for a person).

As mentioned above, the input processing module 208 may ensure that the moving window of time includes a certain number of data points. This may be achieved by replacing any missing or invalid data points with an approximation of what a valid data point would be at that particular point in time. Validity may be determined with reference to a predetermined range of acceptable values. For example, SG values may be invalidated if they do not fall within a predetermined range of values associated with a properly functioning glucose sensor. In some cases, missing data points may result from communication failure. For example, missing SG values may be attributable to connectivity issues between the monitoring device and the computing device or the delivery device. A valid data point may be approximated based on one or more adjacent data points that are valid. For example, a missing/invalid data point may be replaced with the value of an adjacent data point or with the average of the values of two adjacent data points. In some embodiments, approximating a valid data point may be performed if the total number of missing/invalid data points within a moving time window is less than a predetermined number of percentage threshold (e.g., 9 (out of 36) or 25%).

The machine learning model 202 can be implemented as a classifier for detecting whether or not the user is in a postprandial stage (e.g., by detecting whether or not a SG value corresponds to an ongoing glycemic response to a meal). In some embodiments, a binary output 214 may be produced by the machine learning model 202. In some specific embodiments, the classifier may use logistic regression to detect a meal (or absence of meal) based on inputs of SG values and estimated Ip data collected every five minutes (e.g., the most recent 36 samples of SG in the first input vector 204 and the most recent 36 samples of normalized Ip in the second input vector 206). In some scenarios, more recent samples may have more influence on model predictions than older samples. In some specific embodiments, the classifier may include a LSTM model configured to detect a meal (or absence of meal) based on similar inputs of SG and normalized Ip.

In the example of detecting a postprandial stage, the classifier may determine the probability of the postprandial stage being present as each new sample is collected, e.g., every five minutes. If the determined probability is greater than a threshold (e.g., 50%, or higher), the classifier may mark it as a postprandial stage. The probability threshold may be used as a sensitivity parameter for the classifier and can be increased to higher levels (e.g., 70%, 80%, 90%) to achieve higher confidence in detecting postprandial periods or lowered (e.g., 90% to 70%, 50% to 40%) to increase the sensitivity at the expense of false positives.

In some implementations, the probability threshold may be adjusted based on the size of the moving window of time. For instance, to increase the confidence level of whether or not a meal is detected, the size of the moving window may be increased (e.g., four-hour window with 48 samples, rather than a three-hour window with 36 samples). While a larger window may delay the initialization of the meal detection (e.g., it would need to wait four hours to begin automatic real-time meal detection instead of three hours), it may result in higher accuracy and fewer false alarms given the same probability threshold. In some implementations, the probability threshold may be decreased based on a current size of the moving window of time.

Figure 3A:
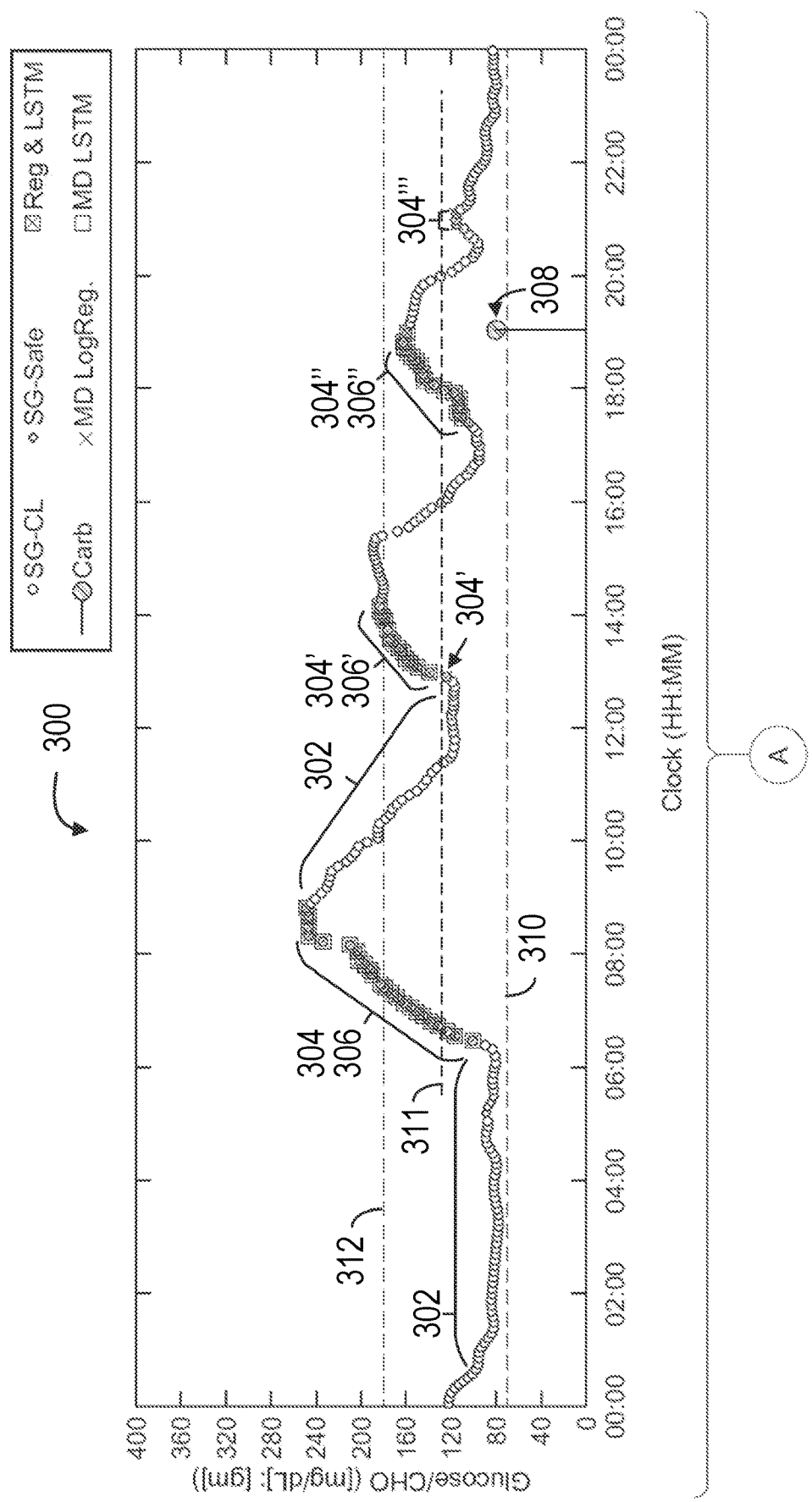
FIG. 3A is an example of a graph illustrating an example of real-time meal detection using a system disclosed herein according to certain embodiments.

FIG. 3A is an example of a graph 300 illustrating an example of real-time meal detection using a system disclosed herein according to certain embodiments.

Circles (and diamonds) represent SG values 302. The SG values 302 are obtained every five minutes in this example. The example graph 300 shows, between approximately 01:00 to 06:00, a series of SG values 302 within a relatively narrow range without much fluctuation, which is indicative of this time period corresponding to an overnight fasting period. Thus, graph 300 shows an overnight fasting glucose level of about 80 mg/dL for this person. The SG values 302 are above a lower glucose threshold 310 (e.g., a hypoglycemia threshold) and below an upper glucose threshold 312 (e.g., a hyperglycemia threshold) during this time period.

The example graph 300 shows SG values with crosses superimposed on top of them between approximately 06:20 and 08:45, representing SG values identified as corresponding to a postprandial stage 304 using a logistic regression model. Similarly, the example graph 300 shows SG values with squares superimposed on top of them between approximately 06:20 and 08:45, representing SG values identified as corresponding to a postprandial stage 306 using a LSTM model. Stated differently, graph 300 shows a glycemic response (to a meal, such as breakfast) that includes the SG values superimposed with crosses and squares during this time period. In various embodiments, the logistic regression model and the LSTM model may each be a classifier and an example of the machine learning model 202 as discussed above with respect to FIG. 2. Although the graph 300 shows the use of multiple models, it should be appreciated that the techniques disclosed herein can be used with any number of models (i.e., one model or a plurality of models). In implementations using multiple models, each model can be used to independently detect meals (as depicted in graph 300), or the models can be used to provide a consensus meal detection (as in the case of an ensemble model).

For postprandial stages 304 and 306, the logistic regression model and the LSTM model have each identified the SG value at approximately 6:20 as the earliest SG value that is part of the glycemic response to the meal. As will be described in greater detail below, this SG value may have been identified based on a variety of criteria, including any number of the following:

whether or not this SG value exceeds a predetermined threshold (e.g., 5 mg/dL above an average fasting glucose level);

whether or not this SG value is higher than its immediate predecessor;

the difference between this SG value and its immediate predecessor;

whether or not this SG value corresponds with an Ip value that is higher than its immediate predecessor;

the difference between this Ip value and its immediate predecessor; and/or whether any other SG values were previously identified as being part of a glycemic response within the moving time window (e.g., within the trailing three hours).

Working backward from this SG value, the onset of the ongoing glycemic response can be identified at approximately 06:05. Thus, the graph 300 shows how quickly the model 202 can detect a meal (e.g., within three SG samples from the onset of the ongoing glycemic response). In this case, this detection may be due in part to the size of the moving time window, which included no other glycemic response when the SG value at approximately 06:20 was identified as being part of a glycemic response. In some cases, how quickly the ongoing glycemic response is detected may depend on how quickly glucose levels increase. Automatic meal detection may happen sooner with a steeper rise of SG values from the onset (such as postprandial stages 304 and 306), or the detection may take longer with slower rising SG values from the onset.

FIG. 3A depicts SG values rising or plateauing between approximately 06:20 and 08:45 in a manner consistent with a glycemic response to a meal. However, after approximately 08:45 and until approximately 13:00, the logistic regression model and the LSTM model no longer detect the glycemic response to the meal, and this is reflected in graph 300 by SG values 302 dropping and plateauing (and not having crosses or squares superimposed) during this time period. The logistic regression model and the LSTM model may each be receiving as input a moving window of the most recent SG values (including those corresponding to at least part of postprandial stages 304 and 306) and Ip values to make the determination of "not a glycemic response to a meal."

At approximately 13:00, an ongoing glycemic response to another meal (e.g., lunch) is identified by the logistic regression model, and between approximately 13:00 and 14:20, the logistic regression model continues to identify SG values included in postprandial stage 304'. Between approximately 13:05 and 14:20, SG values included in postprandial stage 306' are identified by the LSTM model. In this example, the logistic regression model was able to identify the glycemic response earlier than the LSTM model. Nonetheless, both models identified the glycemic response relatively quickly (e.g., within one or two SG samples from the onset of the ongoing glycemic response at approximately 12:55). This may be due in part to the size of the moving time window, which was sized to include an inter-meal fasting period and to exclude any other glycemic response.

Between approximately 17:30 and 19:00, postprandial stages 304" and 306" are respectively identified by the logistic regression model and the LSTM model. Stages 304" and 306" correspond to a glycemic response to yet another meal (e.g., dinner). Similar to the time period between approximately 06:20 and 08:45, both the logistic regression model and the LSTM model were able to detect the glycemic response at the same time (e.g., within two SG samples from the onset of the ongoing glycemic response at approximately 17:20).

The example graph 300 also shows carbohydrate intake 308 announced by a user, indicated by a tall stem at approximately 19:00. As will be described in greater detail below, meal announcements can be compatible with systems employing automatic real-time meal detection. As used herein, a "meal announcement" broadly refers to user input indicative of a meal occurrence. Non-limiting examples of a meal announcement include input indicating that a user commanded a meal bolus and/or input corresponding to manual entry of an estimated amount of carbohydrate intake.

At approximately 21:00, postprandial stage 304' is identified by the logistic regression model. It may be that postprandial stage 304''' corresponds to a glycemic response to a snack. Notably, the LSTM model did not identify any postprandial stage at this time. Depending on the sensitivity of the classifier, the postprandial stage 304''' (or any of the postprandial stages discussed above) may not be identified or detected by the logistic regression model or the LSTM model.

Figure 3B:
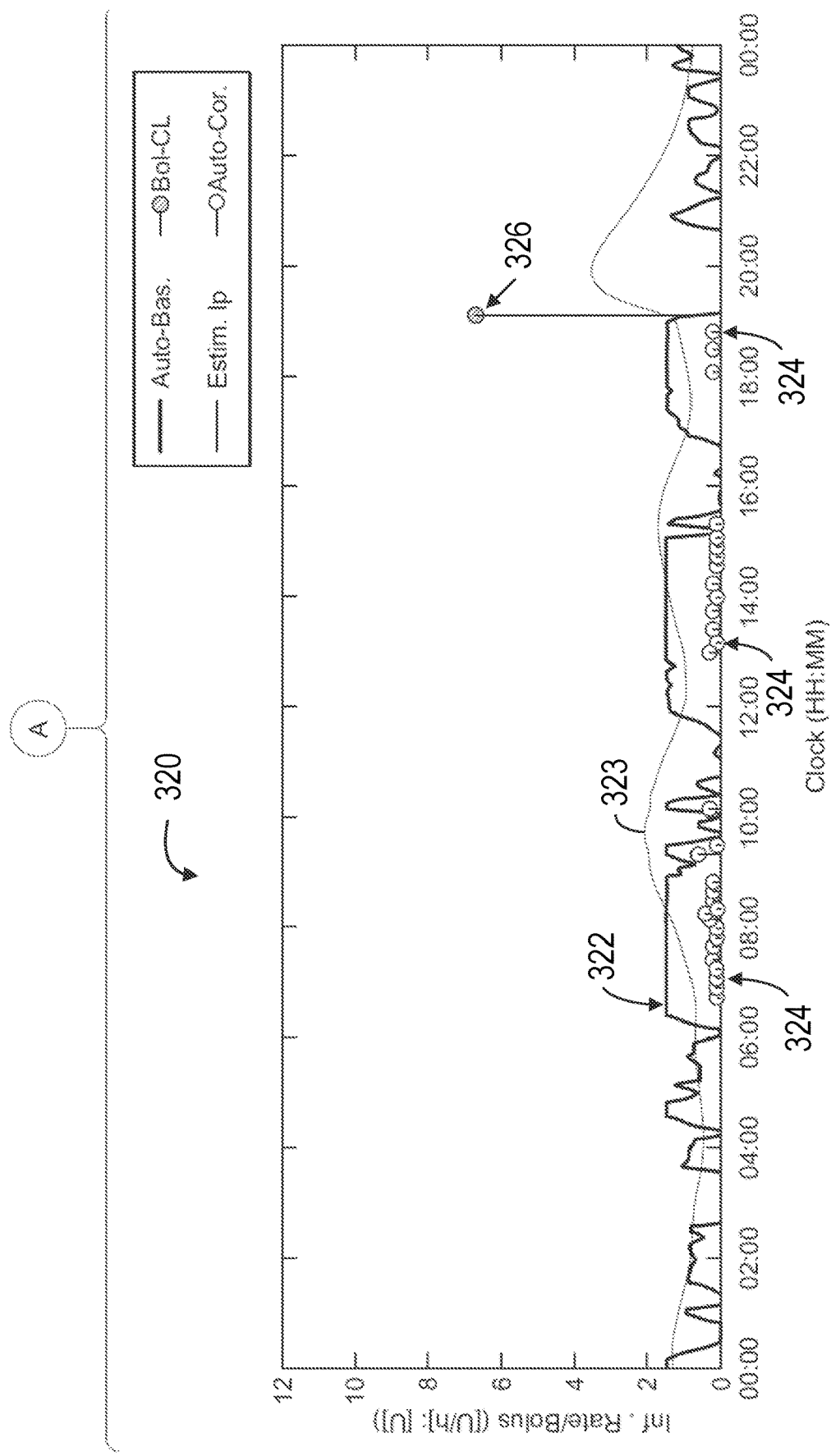
FIG. 3B is an example of a graph that correlates in time to the example of the graph of FIG. 3A, the graph showing insulin delivery information and estimated plasma insulin concentration.

FIG. 3B is an example of a graph 320 that correlates in time to the example of the graph 300 of FIG. 3A. The example graph 320 shows insulin delivery information including basal dosages 322, correction boluses 324, and meal bolus 326; and estimated plasma insulin concentration 323.

The example graph 320 shows a thick line representing amounts of basal dosages 322 as a function of time. In some cases, the basal dosages 322 may be delivered automatically based on a difference between the current SG value and a target SG value (e.g., by a closed-loop control system employing proportional-integral-derivative (PID) control or model predictive control (MPC)). In some cases, the basal dosages 322 may be delivered automatically (e.g., by an open-loop system) based on pre-programmed basal delivery rates and/or schedules.

The example graph 320 further shows a thin line representing estimated plasma insulin concentration 323 over time. In some implementations, insulin delivery information (e.g., basal dosages 322, correction boluses 324, and/or meal bolus 326) may be tracked by a delivery device 102 and provided to a computing device 106 and/or a computing system 108. The estimated plasma insulin concentration 323 may be derived from the insulin delivery information using, e.g., a pharmacodynamic model such as that represented by Eqns. 1 and 2.

The example graph 320 further shows unshaded circles with stems of varying heights representing varying amounts of correction boluses 324. Whether or not correction boluses 324 are delivered can depend on a variety of criteria, including any number of the following:

whether or not the current SG value exceeds a target SG value (e.g., a target value that is used for correction boluses and/or that is separate from the target value used for basal dosages);

whether or not the maximum basal delivery rate has been reached; and/or whether or not the amount of insulin on board (JOB) is less than the amount of insulin to be delivered as a correction bolus.

As mentioned above, a correction bolus can be implemented as a correction micro-bolus that is smaller than a meal bolus (e.g., meal bolus 326) and can be similar in size to a basal dosage. In some implementations, there may be an upper limit on the size of a correction bolus. For example, either the current SG value or a maximum SG value (whichever is lesser) may be used to calculate the amount of insulin to be delivered as a correction bolus (e.g., based on the difference between a target SG value and the current/maximum SG value.

As depicted in graph 320, one or more automatic correction boluses 324 may be administered to the user instead of or in addition to a meal bolus 326. In the example of FIG. 3B, responsive to detection of the first meal, a plurality of correction boluses 324 are delivered in lieu of a meal bolus, and responsive to detection of the third meal, one or more correction boluses 324 are delivered prior to a meal bolus 326.

Among the advantages of automatically delivering correction boluses 324 is the ability to mitigate the risk of delivering insulin in error (e.g., in response to an inaccurate meal detection). Conceptually, a plurality of correction boluses can be thought of as collectively constituting a meal bolus. Thus, by preventing further deliveries of correction boluses, it is possible to limit erroneous delivery to the equivalent of a partial meal bolus. Moreover, a correction bolus that is delivered in error can be metabolized much more quickly (e.g., by temporarily suspending basal dosages) than a meal bolus that is delivered in error. Another advantage of automatically delivering correction boluses

324 is that instead of determining an insulin delivery amount based on carb counting or some other error-prone approach for estimating meal content, the insulin delivery amount can be dynamically determined in several portions as SG values are obtained in real time. Yet another advantage is that in conjunction with automatic meal detection, automatically delivery of correction boluses 324 enables a fully automated insulin delivery system (e.g., an artificial pancreas).

To optimize the use of correction boluses 324 instead of or in addition to a meal bolus, various modifications can be implemented temporarily (e.g., for a predetermined amount of time after identification of the earliest SG value corresponding to the glycemic response). In particular, to reduce the overall number of correction boluses 324 and to deliver more insulin closer to the start of a meal, the amount of each correction bolus can be temporarily increased in response to meal detection. For example, a parameter (e.g., a person-specific ISF) used to calculate a correction bolus may be temporarily adjusted (e.g., decreased). Additionally or alternatively, the target SG value for correction boluses may be temporarily reduced.

The example graph 320 further shows a shaded circle with a tall stem representing the amount of the meal bolus 326. Notably, the meal bolus 326 is a late meal bolus that corresponds in time with the late announcement of carbohydrate intake 308 of FIG. 3A. Thus, three correction boluses 324 were previously delivered responsive to meal detection. Insulin overdelivery can result when a meal bolus is delivered in addition to correction boluses. Accordingly, to avoid insulin overdelivery, the amount of a late meal bolus (e.g., a bolus dosage commanded after delivery of correction boluses but within a predetermined time period following meal detection) may be calculated by subtracting the amounts of any correction boluses that were previously delivered in response to detection of the same meal.

Figure 3C:
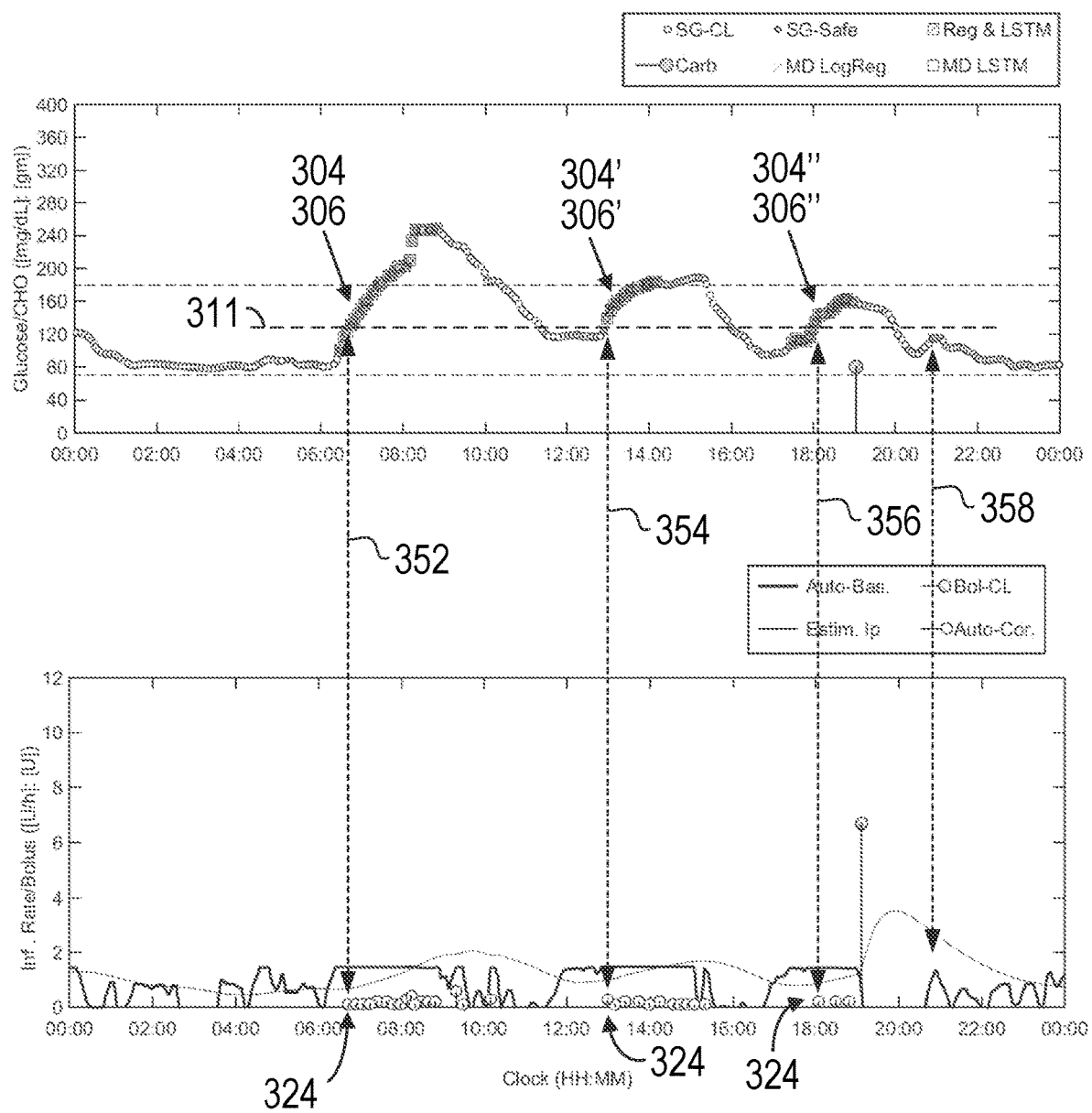
FIG. 3C shows a juxtaposition of the examples of graphs of FIGS. 3A and 3B.

FIG. 3C shows a juxtaposition of the examples of graphs 300 and 320 of FIGS. 3A and 3B. Notably, delivery of correction boluses 324 for the first meal commences at time 352. Similarly, deliveries of correction boluses 324 for the second and third meals respectively commence at times 354 and 356. However, there are no correction boluses at time 358. This is due (at least in part) to the use of a target SG value (corresponding to threshold 311) for correction boluses.

As can be observed in FIGS. 3A-3C, both types of classifiers (logistic regression model and LSTM model) were able to detect or otherwise identify postprandial periods for each of the three major meals (breakfast, lunch, and dinner) within three SG values of the onset of the respective ongoing glycemic response and without any user input. Such automatic real-time detection of postprandial periods may have various practical applications. For example, it can be used to implement a fully automated diabetes management system (e.g., an artificial pancreas) that automatically delivers therapy responsive to meal detection. As another example, automatic real-time meal detection can be used for administering therapy in a more manual fashion by causing presentation of a notification (e.g., a visual and/or audio alert) indicative of meal detection. The notification may be presented at the delivery device 102 or the computing device 106 to remind a user (e.g., a patient or a caretaker) to administer therapy. The above practical applications of automatic real-time meal detection are illustrative examples and may not be so limited.

Example Methods

Figure 4:
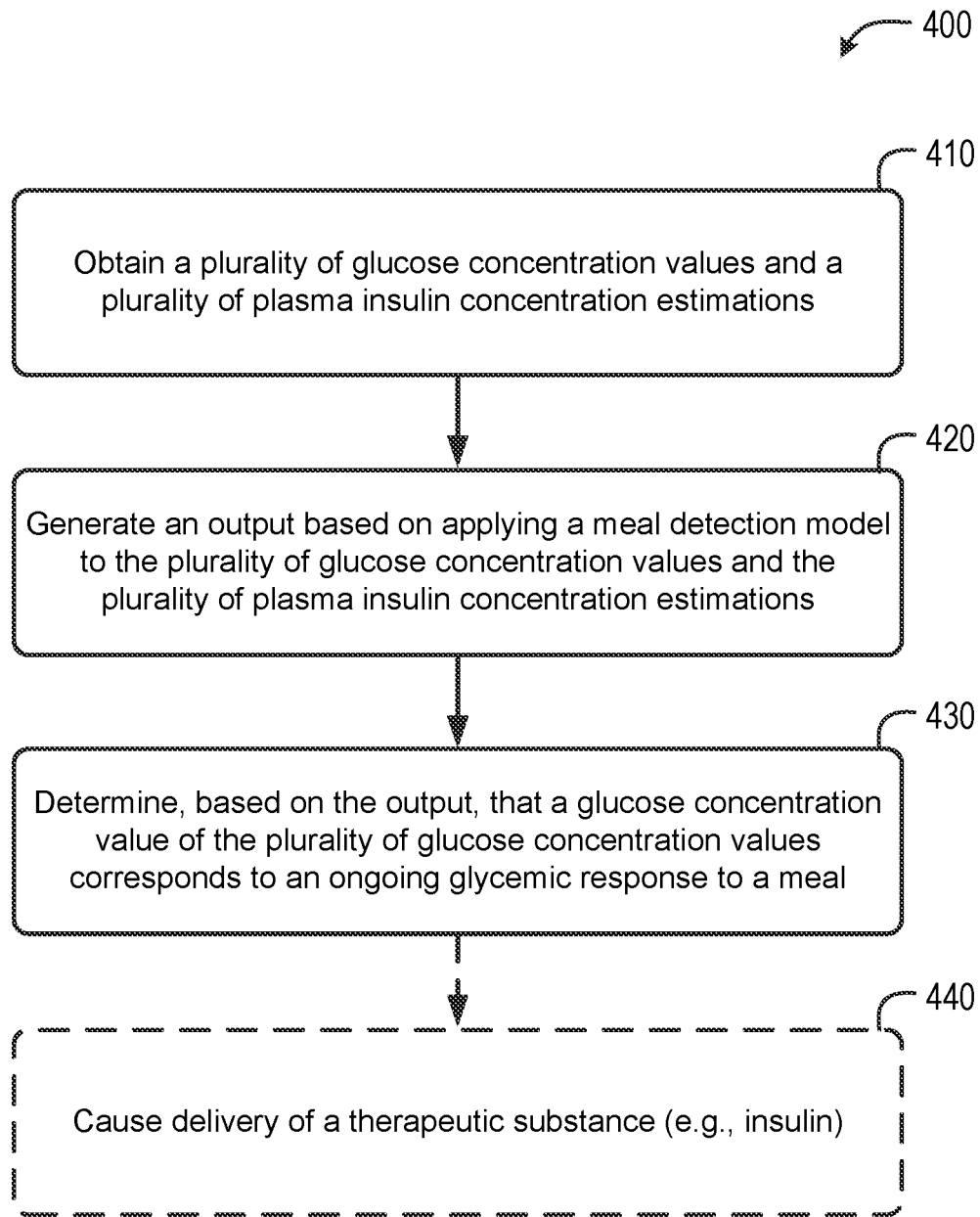
FIG. 4 is a flow diagram illustrating an example of a method for automatic real-time meal detection, according to some embodiments.

FIG. 4 is a flow diagram illustrating an example of a method 400 for automatic real-time meal detection, according to some embodiments. The method 400 may be performed by one or more devices (e.g., device 102, device 104, device 106, and/or system 108). Each of the one or more devices may include hardware and/or software components, such as, for example, one or more processors (e.g., a microcontroller and/or a microprocessor) and/or one or more processor-readable media storing instructions which, when executed by one or more processors, cause performance of one or more operations. It should also be noted that the method 400 may be performed in any suitable order, not necessarily the order depicted in FIG. 4. Further, the method 400 may include additional or fewer operations than those depicted in FIG. 4.

As depicted in block 410, the method 400 may include obtaining a plurality of glucose concentration values and a plurality of plasma insulin concentration estimations for a user (e.g., a patient using a computing system for performing the method 400). The plurality of glucose concentration values may be obtained based on data communicated from delivery device 102, monitoring device 104, computing device 106, and/or computing system 108. The plurality of plasma insulin concentration estimations may be obtained based on data communicated from delivery device 102, computing device 106, and/or computing system 108.

Each glucose concentration value may be a blood glucose concentration estimation derived based on an interstitial glucose measurement. In some embodiments, the plurality of glucose concentration values may undergo processing that involves replacing at least one invalid or missing glucose concentration value (e.g., invalid due to falling outside a predetermined range or missing due to a communication failure) with at least one valid or estimated glucose concentration value (e.g., based on copying an adjacent value that is valid or interpolating a value based on adjacent values). However, the processing may be performed responsive to determining that a threshold number of the plurality of glucose concentration values are valid (e.g., fall within a predetermined range).

Each plasma insulin concentration estimation may be obtained based on applying an insulin absorption model to insulin delivered exogenously to the user. In some embodiments, the plurality of plasma insulin concentration estimations may undergo processing that involves normalization based on dividing by 50% of a six-day median insulin total daily dose.

Each glucose concentration value may correspond with a respective plasma insulin concentration estimation. For example, each glucose concentration value may correspond in time with a respective plasma insulin concentration estimation to form a plurality of time-corresponding pairs of glucose concentration values and plasma insulin concentration estimations. In some embodiments, glucose concentration values and plasma insulin concentration estimations may be stored in a single data structure (e.g., a matrix containing multiple rows and/or columns) that reflects their corresponding relationship. In some other embodiments, glucose concentration values and plasma insulin concentration estimations may be stored in separate data structures (e.g., separate vectors) that reflect their corresponding relationship. For example, a time-corresponding pair may be implemented as a glucose concentration value stored at a particular position within a first vector and a corresponding plasma insulin concentration estimation stored at the same position within a second vector.

As depicted in block 420, the method 400 may include generating an output based on applying a meal detection model to the plurality of glucose concentration values and the plurality of plasma insulin concentration estimations. Application of the meal detection model may be performed at delivery device 102, computing device 106, or computing system 108. For example, computing system 108 may generate the meal detection model and communicate it to delivery device 102 or computing device 106, where application of the model can be performed. The meal detection model may be a machine learning model trained to detect an ongoing glycemic response to a meal. The output of the meal detection model may be a binary output (e.g., "glycemic response to a meal" or "not a glycemic response to a meal"). In some embodiments, generating the output may include obtaining a probability that at least a subset of the plurality of glucose concentration values corresponds to the glycemic response to the meal; comparing the probability to a probability threshold (e.g., 50%); and making a binary determination (e.g., "glycemic response to a meal" or "not a glycemic response to a meal") based on the comparing.

In some embodiments, the machine learning model may be operable as a classifier. In some implementations, the classifier may include a logistic regression model. In some implementations, the classifier may include a LSTM recurrent neural network model.

In some embodiments, the glucose concentration values and the plasma insulin concentration estimations are provided to a meal detection model in a manner that reflects their corresponding relationship. For example, a plurality of time-corresponding pairs may be provided to the meal detection model as a first input vector and a second input vector. The first input vector may include least a portion of the plurality of glucose concentration values, and the second input vector may include at least a portion of the plurality of plasma insulin concentration estimations. The first input vector and the second input vector may each include a current data point and a predetermined number of past data points (e.g., the 35 most recent SG or Ip values) within a moving window of time (e.g., three hours) that is sized to include a fasting period and to exclude a period of postprandial glucose level increase prior to the fasting period.

As depicted in block 430, the method 400 may include determining, based on the output, that a glucose concentration value of the plurality of glucose concentration values corresponds to an ongoing glycemic response to a meal. In some embodiments, the determining may include identifying an earliest glucose concentration value that was identified, based on applying the meal detection model to the plurality of glucose concentration values, as being part of the ongoing glycemic response to the meal; evaluating backward in time from the earliest glucose concentration value to identify an onset of an increasing glucose trend within three glucose concentration values from the earliest glucose concentration value identified; and determining that the onset of the increasing glucose trend corresponds to an onset of the ongoing glycemic response to the meal. An increasing trend may refer to obtaining a higher value compared to an earlier value within a series of two or more values. In some cases, the series of two or more values may comprise consecutively higher values (e.g., three values with the second higher than the first and the third higher than the second). In some cases, the series may comprise consecutive values that are equal (e.g., three values with the second higher than the first and the third equal to the second). Thus, a determination can be made that the onset of the increasing glucose trend corresponds to the onset of the ongoing glycemic response to the meal. As alluded to above, in some cases, the steepness of the trend may influence how early the determination can be made.

As depicted in block 440, the method 400 may optionally include causing delivery of a therapeutic substance. In some embodiments, the therapeutic substance may be delivered to at least partially counteract the glycemic response to the meal. For example, the therapeutic substance may be a meal bolus of insulin and/or one or more correction boluses of insulin constituting at least part of a meal bolus, and depending on the amount of insulin delivered, the insulin may restore glucose levels to pre-meal levels.

In some implementations, a therapeutic substance delivery device (e.g., device 102) may cause delivery of the therapeutic substance based on generating and communicating one or more signals to an actuator associated with a therapeutic substance reservoir. For example, the actuator may be a motor that is mechanically coupled to the reservoir via a gear train and a plunger rod so as to push the therapeutic substance out of the reservoir; or the actuator may be a microelectromechanical system (MEMS) pump that is fluidically coupled to the reservoir so as to pull the therapeutic substance out of the reservoir. Each signal of the one or more signals may be an electrical signal indicative of an amount of the therapeutic substance to be delivered (e.g., a number of motor rotations or a number of diaphragm deflections).

In some implementations, a computing device (e.g., device 106) may cause delivery of the therapeutic substance based on communicating one or more signals to a therapeutic substance delivery device (e.g., device 102). Each signal of the one or more signals may be an electrical/electromagnetic signal that is indicative of an amount of the therapeutic substance to be delivered (e.g., a signal indicating this amount) or that commands the delivery device to determine this amount, thereby causing the delivery device may generate and communicate (to an actuator of the delivery device) a signal indicative of this amount.

In some implementations, causing delivery of the therapeutic substance may include temporarily decreasing a target glucose value (e.g., a target SG value for correction boluses). This may be performed by the delivery device or the computing device. The target glucose value may be for a closed-loop mode of the delivery device, the closed-loop mode being configured for automated delivery of the therapeutic substance based on a difference between the current glucose value and the target glucose value. The delivery device or the computing device may use the reduced target glucose value to determine an amount of insulin for delivery, and any of the aforementioned signals may be indicative of this amount.

In some embodiments, a therapeutic substance delivery device (e.g., device 102), a computing device (e.g., device 106), and/or a remote/cloud computing system (e.g., system 108) may cause generation of a notification indicative of the meal detection. Such a notification may be, for example, a visual and/or audio alert to remind a user or a caretaker to administer a meal bolus. The notification may be presented at the therapeutic substance delivery device and/or the computing device. For example, when computing device 106 detects a meal, device 106 may generate and present a notification. Additionally or alternatively, device 106 may generate and communicate a signal to delivery device 102, thereby causing device 102 to generate and present a notification.

Figure 5:
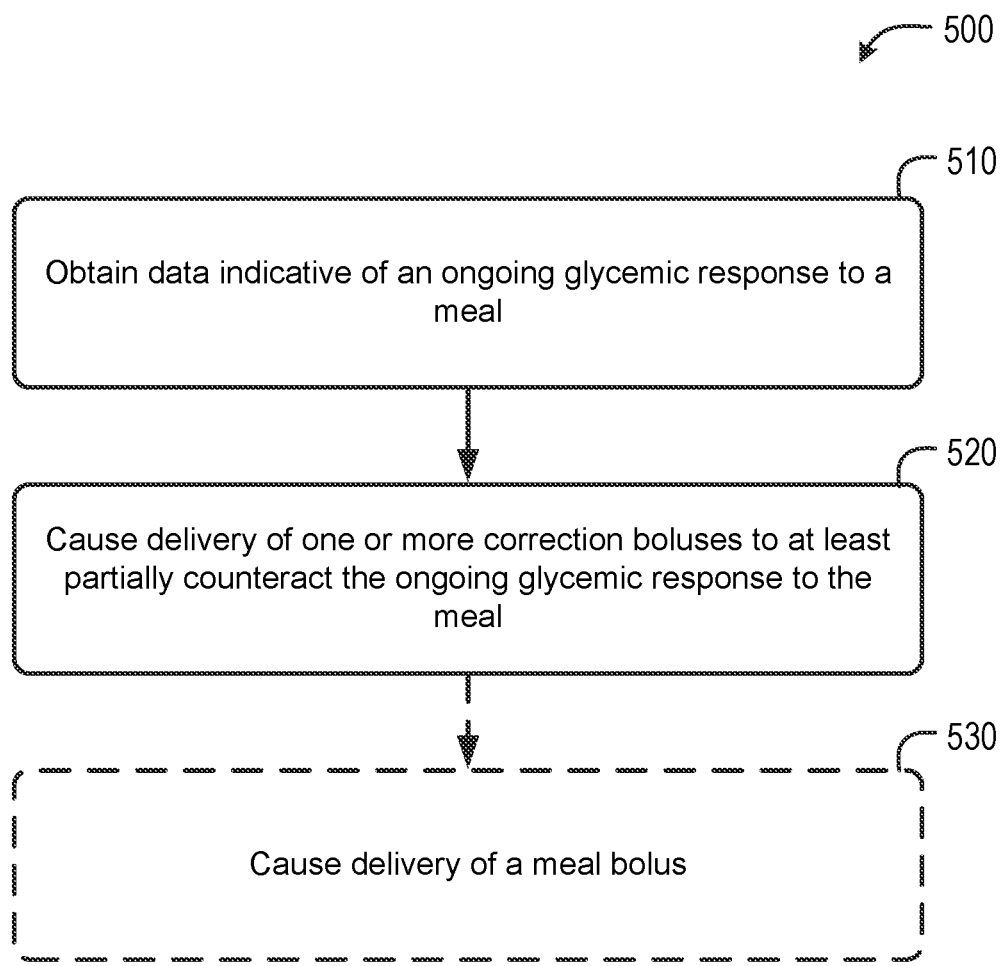
FIG. 5 is a flow diagram illustrating an example of a method for automatic meal-time delivery of correction boluses, according to some embodiments.

FIG. 5 is a flow diagram illustrating an example of a method 500 for automatic meal-time delivery of correction boluses, according to some embodiments. The method 500 may be performed by one or more devices (e.g., device 102, device 104, device 106, and/or system 108). Each of the one or more devices may include hardware and/or software components, such as one or more processors (e.g., a microcontroller and/or a microprocessor) and/or one or more processor-readable media storing instructions which, when executed by one or more processors, cause performance of one or more operations.

It should also be noted that the operations of the method 500 may be performed in any suitable order, not necessarily the order depicted in FIG. 5. Further, the method 500 may include additional or fewer operations than those depicted in FIG. 5.

As depicted in block 510, the method 500 may include obtaining data indicative of an ongoing glycemic response to a meal. In some embodiments, the data may include an output generated by a meal detection model. In some embodiments, the output may be generated based on applying the meal detection model to a plurality of glucose concentration values corresponding with a plurality of plasma insulin concentration estimations.

As depicted in block 520, the method 500 may include causing delivery of one or more correction boluses to at least partially counteract the ongoing glycemic response to the meal. In some embodiments, block 520 may correspond to block 440 of FIG. 4.

Similar to block 440, in some implementations, a therapeutic substance delivery device (e.g., device 102) may cause delivery of the one or more correction boluses based on generating and communicating one or more signals to an actuator associated with a therapeutic substance (e.g., insulin) reservoir. Each signal of the one or more signals may be an electrical signal indicative of an amount of the therapeutic substance to be delivered (e.g., a number of motor rotations or a number of diaphragm deflections).

Similar to block 440, in some implementations, a computing device (e.g., device 106) may cause delivery of the one or more correction boluses based on communicating one or more signals to a therapeutic substance delivery device (e.g., device 102). Each signal of the one or more signals may be an electrical/electromagnetic signal that causes the delivery device to generate and communicate a signal (to an actuator of the delivery device) indicative of an amount of the therapeutic substance to be delivered.

In some embodiments, the therapeutic substance delivery device or the computing device may temporarily reduce a target glucose value that is used in a closed-loop mode of the therapeutic substance delivery device (e.g., a target glucose value that is used for determining amounts of correction boluses and that is separate from a target glucose value used for determining amounts of basal dosages). More specifically, the target glucose value may be reduced from a first glucose value (e.g., A mg/dL) to a second glucose value (e.g., B mg/dL). The difference between the current glucose value (e.g., C mg/dL) and the reduced target glucose value (e.g., B mg/dL) may be used to determine an amount of a correction bolus. When the glycemic response is no longer detected, the reduced target glucose value may be increased from the second glucose value (e.g., B mg/dL) to the first glucose value (e.g., A mg/dL).

Additionally or alternatively, the therapeutic substance delivery device or the computing device may temporarily increase the size of the one or more correction boluses. More specifically, a parameter (e.g., ISF) may be reduced from a first parameter value (e.g., A) to a second parameter value (e.g., B). The reduced parameter may be used to determine an amount of a correction bolus. When the glycemic response is no longer detected, the reduced parameter may be increased from the second parameter value (e.g., B) to the first parameter value (e.g., A).

As mentioned above, the one or more correction boluses may be delivered based on one or more signals communicated to a delivery device and/or one or more signals communicated to an actuator of the delivery device. Each of these signals may be indicative of an amount of a correction bolus that was calculated based on a reduced target glucose value and/or a reduced parameter.

As depicted in optional block 530, the method 500 may include causing delivery of a meal bolus after causing delivery of the one or more correction boluses. Similar to blocks 440 and 520, in some implementations, a delivery device may cause delivery of the meal bolus, and in some implementations, a computing device may cause delivery of the meal bolus. Regardless of which device(s) are involved, the meal bolus is a late meal bolus in that the one or more correction boluses were previously delivered to at least partially counteract the glycemic response to the same meal. However, to avoid insulin overdelivery, the size of the late meal bolus can be reduced to account for the one or more correction boluses. For example, the delivery device or the computing device may determine a potential amount for the meal bolus (e.g., an amount calculated based on a meal announcement), determine a total amount of insulin delivered as the one or more correction boluses, and subtract this total amount from the potential amount to determine a reduced amount for the meal bolus. To cause delivery of the late meal bolus in the reduced amount, the delivery device and/or the computing device may generate and communicate (e.g., to an actuator and/or a delivery device) a signal indicative of the reduced amount.

Example Apparatus

In some embodiments, therapy may be effected based on communicating a therapy determination toward a therapy delivery device. A non-limiting example of such a device is described below in connection with FIG. 6, which depicts an example insulin delivery device 600, in accordance with aspects of the present disclosure.

Figure 7:
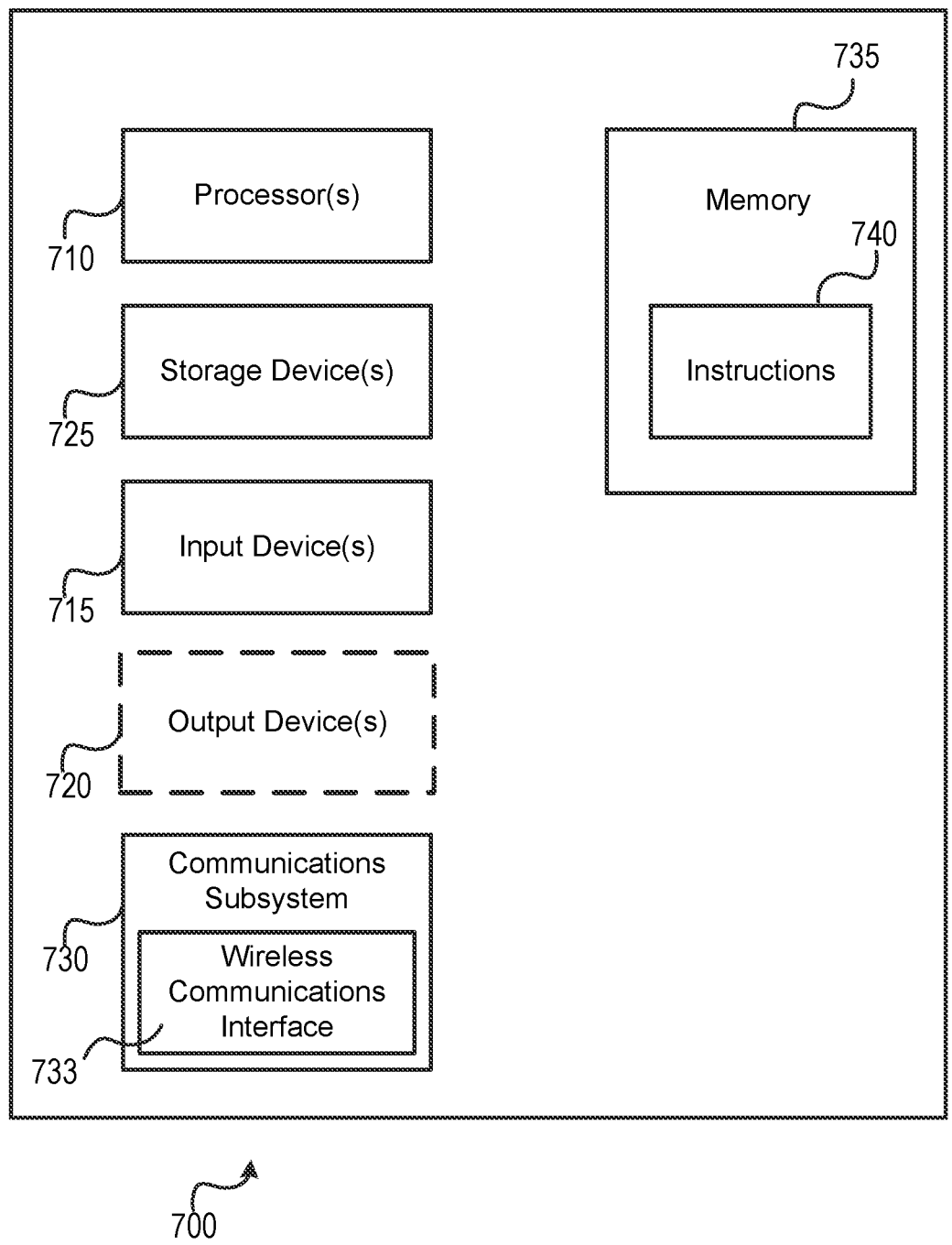
FIG. 7 is a block diagram of an example of a computer system, which can be utilized in embodiments as described herein.

As mentioned above, therapy determinations may be communicated toward an insulin delivery device 600 (e.g., from a cloud computing system 108 via an intermediary computing device 106 communicatively coupled to the device 600). The insulin delivery device 600 may be an example of the delivery device 102 as described throughout this disclosure. In such a device, insulin delivery may be performed based on internal communication between a central computing module (e.g., a microcontroller for device 600 as a whole) and an insulin delivery module (e.g., including a motor and a pump). For instance, insulin delivery may be caused by the central computing module communicating a delivery command in the form of an electrical signal that travels via a communication fabric to the insulin delivery module. The central computing module may also be configured to communicate (e.g., via a transceiver) with a computing device (e.g., 106, FIG. 1) communicatively coupled to a remote or cloud computing system (e.g., 108, FIG. 1). The insulin delivery device 600 may communicate various event data (e.g., meal data, exercise data, and/or insulin delivery data) toward the remote or cloud computing system, which may communicate insulin delivery determinations toward the insulin delivery device 600, in some implementations. FIG. 7 further illustrates components which can be included in the insulin delivery device 600.

Figure 6:
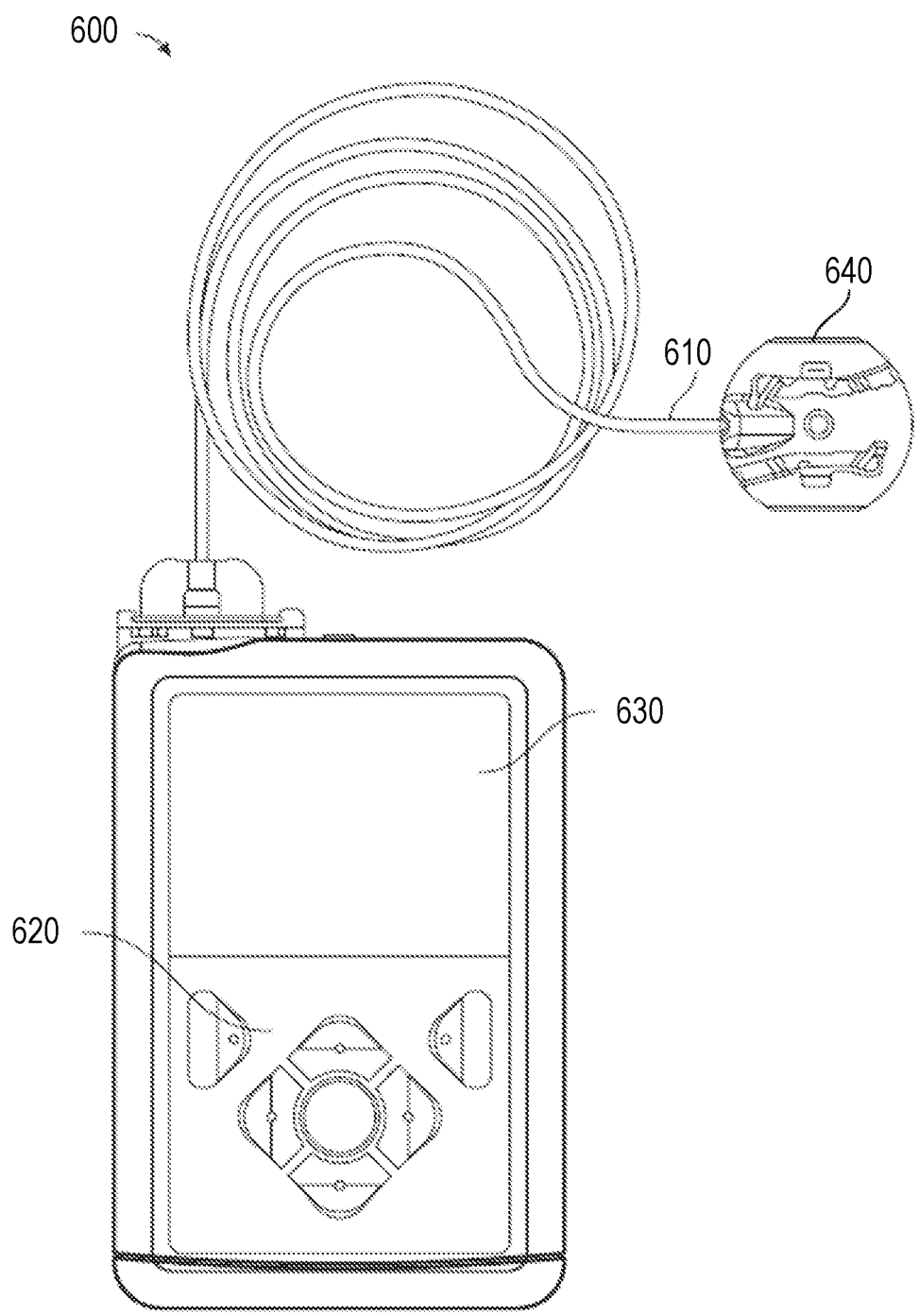
FIG. 6 is a diagram of an example of an insulin delivery device, in accordance with aspects of the present disclosure.

The insulin delivery device 600 can provide fast-acting insulin through a small tube 610 configured for fluidic connection with a cannula (not shown). The cannula may be inserted subcutaneously under a fixation dressing 640 that includes an inlet for the tube 610, an outlet for the cannula, and an adhesive surface for affixing the dressing 640 to skin. The device 600 can deliver at least two types of dosages—a basal dosage, which can be delivered periodically (e.g., every five minutes) in tiny amounts throughout the day and night, and a bolus dosage to cover an increase in blood glucose from meals and/or to otherwise correct high blood glucose levels. The depicted insulin delivery device 600 includes a user interface having button elements 620 that can be manipulated to administer a bolus of insulin, to change therapy settings, to change user preferences, to select display features, and the like. The insulin delivery device 600 also includes a display device 630 that can be used to present various types of information or data to the user (such as a notification or an alert of the type described above). In accordance with aspects of the present disclosure, a user of the insulin delivery device 600 may use the button elements 620 to input certain event data (e.g., event type, event start time, event details, etc.), and the user inputs can be confirmed using the display device 630. The depicted insulin delivery device 600 of FIG. 6 is merely provided by way of example, and other types of insulin delivery devices and other techniques different from those described above are contemplated to be within the scope of the present disclosure.

FIG. 7 is a block diagram of an embodiment of a computer system 700, which can be utilized in embodiments as described herein. It should be noted that FIG. 7 is meant only to provide a generalized illustration of various components, any or all of which may be utilized as appropriate. In addition, it can be noted that components illustrated by FIG. 7 can be localized to a single device (e.g., delivery device 102, monitoring device 104, computing device 106, or computing system 108) and/or distributed among various networked devices, which may be disposed at different geographical locations.

In some embodiments, the computer system 700 may include hardware elements that can be electrically coupled via a bus (or may otherwise be in communication, as appropriate). The hardware elements may include processor(s) 710, which may comprise, without limitation, one or more microcontroller(s), one or more microprocessor(s), one or more general-purpose processors, one or more special-purpose processors (such as digital signal processing chips, graphics acceleration processors, and/or the like), and/or other processing structure, which can be configured to perform one or more of the methods or functionalities described herein.

In some embodiments, the computer system 700 also may include one or more input devices 715, which may comprise, without limitation, button elements 620, a microphone, a glucose sensor, and/or the like. The computer system 700 may also include one or more output devices 720, which may comprise without limitation a display device (e.g., 630), a speaker, a buzzer, and/or the like.

In some embodiments, the computer system 700 may further include one or more non-transitory storage devices 725, which can include, without limitation, local and/or network accessible storage, and/or may comprise, without limitation, a disk drive, a drive array, an optical storage device, a solid-state storage device, such as a read-access memory (RAM) and/or read-only memory (ROM), which can be programmable, flash-updateable, and/or the like. Such storage devices may be configured to implement any appropriate data stores, including without limitation, various file systems, database structures, and/or the like. Such data stores may include database(s) and/or other data structures used to store and administer messages and/or other information to be sent to one or more other components or external devices.

In some embodiments, the computer system 700 may also include a communications subsystem 730, which may implement wireless communication technologies managed and controlled by a wireless communication interface 733. Additionally or alternatively, communications subsystem 730 may implement wired technologies (such as Ethernet, coaxial communications, universal serial bus (USB), or the like). The wireless communication interface 733 may comprise one or more wireless transceivers that may send and receive wireless signals (e.g., signals according to Bluetooth®, Bluetooth Low Energy (BLE)). Thus, the communications subsystem 730 may comprise a modem, a network card (wireless or wired), an infrared communication device, a wireless communication device, and/or a chipset, and/or the like, which may enable the computer system 700 to communicate with any device discussed with respect to FIG. 1, including delivery device 102, monitoring device 104, computing device 106, and/or a cloud computing system 108 as described herein. Hence, the communications subsystem 730 may be used to receive and send data (e.g., SG, Ip, insulin delivery information) as described in the embodiments herein.

In some embodiments, the computer system 700 will further comprise a working memory 735, which may comprise a RAM or ROM device, as described above. Software elements, shown as being located within the working memory 735, may comprise computer-readable and computer-executable instructions 740; device drivers; executable libraries; and/or other code, which may comprise computer programs used in various embodiments and/or may be designed to implement methods and/or configure systems in accordance with embodiments described herein. Merely by way of example, one or more operations described with respect to the methods or functionalities discussed above might be implemented as code and/or instructions executable by a computer (and/or a processor within a computer). Such code and/or instructions can be used to configure and/or adapt a general-purpose computer (or other device) to perform one or more operations in accordance with the described methods.

In some embodiments, a set of these instructions and/or code may be stored on a non-transitory computer-readable storage medium, such as the storage device(s) 725 described above. In some cases, the storage medium might be incorporated within a computer system, such as computer system 700. In other embodiments, the storage medium might be separate from a computer system (e.g., a removable medium, such as an optical disc) and/or provided in a downloadable installation package, such that the storage medium can be used to program, configure, and/or adapt a general purpose computer with the instructions and/or code stored thereon. These instructions might take the form of executable code, which is executable by the computer system 700, and/or might take the form of source and/or installable code, which, upon compilation and/or installation on the computer system 700 (e.g., using any of a variety of generally available compilers, installation programs, compression/decompression utilities, etc.), then takes the form of executable code.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to like elements throughout the description of the figures.

Any of the herein described techniques, operations, methods, programs, algorithms, or codes may be converted to, or expressed in, a programming language or computer program embodied on a computer, processor, or machine-readable medium. The terms "programming language" and "computer program," as used herein, each include any language used to specify instructions to a computer or processor, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been depicted in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for automatic real-time meal detection, the system comprising:
   one or more processors; and
   one or more processor-readable media storing instructions which, when executed by the one or more processors, cause performance of one or more operations including:
      obtaining a plurality of glucose concentration values and a plurality of plasma insulin concentration estimations, each glucose concentration value of the plurality of glucose concentration values corresponding in time with a respective plasma insulin concentration estimation of the plurality of plasma insulin concentration estimations to form a plurality of time-corresponding pairs of glucose concentration values and plasma insulin concentration estimations;
      generating an output based on applying a meal detection model to the plurality of glucose concentration values and the plurality of plasma insulin concentration estimations; and
      determining, based on the output, that a glucose concentration value of the plurality of glucose concentration values corresponds to an ongoing glycemic response to a meal.

2. The system of claim 1, wherein the instructions further cause performance of one or more operations including causing delivery of insulin to at least partially counteract the ongoing glycemic response to the meal.

3. The system of claim 2, wherein the causing the delivery of insulin comprises communicating one or more signals to an insulin delivery device.

4. The system of claim 2, wherein the causing the delivery of insulin comprises temporarily decreasing a target glucose value for a closed-loop mode of an insulin delivery device, the closed-loop mode configured for automated delivery of the insulin based on the target glucose value.

5. The system of claim 2, wherein the causing the delivery of insulin comprises communicating one or more signals to an actuator associated with an insulin reservoir.

6. The system of claim 2, wherein the delivered insulin comprises a meal bolus.

7. The system of claim 2, wherein the delivered insulin comprises one or more correction boluses constituting at least part of a meal bolus.

8. The system of claim 1, wherein the instructions further cause performance of one or more operations including causing generation of a notification indicative of the meal detection.

9. The system of claim 1, wherein the plurality of time-corresponding pairs are provided to the meal detection model as a first input vector and a second input vector, the first input vector comprising at least a portion of the plurality of glucose concentration values, the second input vector comprising at least a portion of the plurality of plasma insulin concentration estimations, each of the first input vector and the second input vector including a predetermined number of past data points within a moving window of time.

10. The system of claim 9, wherein the moving window of time is sized to include a fasting period and to exclude a period of postprandial glucose level increase prior to the fasting period.

11. The system of claim 1, wherein determining that the glucose concentration value of the plurality of glucose concentration values corresponds to the ongoing glycemic response to the meal comprises:
   identifying an earliest glucose concentration value that was identified, based on applying the meal detection model to the plurality of glucose concentration values, as being part of the ongoing glycemic response to the meal;
   evaluating backward in time from the earliest glucose concentration value to identify an onset of an increasing glucose trend within three glucose concentration values from the earliest glucose concentration value identified; and determining that the onset of the increasing glucose trend corresponds to an onset of the ongoing glycemic response to the meal.

12. The system of claim 1, wherein the obtaining the plasma insulin concentration estimations comprises applying an insulin absorption model to insulin delivered exogenously to a user.

13. The system of claim 1, wherein generating the output comprises:
obtaining a probability that at least a subset of the plurality of glucose concentration values corresponds to the ongoing glycemic response to the meal;
comparing the probability to a probability threshold; and
making a binary determination based on the comparing.

14. The system of claim 1, wherein:
the meal detection model comprises a machine learning model operable as a classifier; and
the classifier comprises a logistic regression model or a long short-term memory (LSTM) recurrent neural network model.

15. The system of claim 1, wherein the obtaining the plurality of plasma insulin concentration estimations comprises normalizing the plurality of plasma insulin concentration estimations based on a median insulin total daily dose.

16. The system of claim 1, wherein the obtaining the plurality of glucose concentration values comprises, responsive to determining that a threshold number of the plurality of glucose concentration values are valid, replacing at least one invalid glucose concentration value with at least one valid or estimated glucose concentration value.

17. The system of claim 1, wherein each glucose concentration value is a blood glucose concentration estimation based on an interstitial glucose measurement.

18. A processor-implemented method comprising:
obtaining a plurality of glucose concentration values and a plurality of plasma insulin concentration estimations, each glucose concentration value corresponding in time with a respective plasma insulin concentration estimation to form a plurality of time-corresponding pairs of glucose concentration values and plasma insulin concentration estimations;
generating an output based on applying a meal detection model to the plurality of glucose concentration values and the plurality of plasma insulin concentration estimations; and
determining, based on the output, that a glucose concentration value of the plurality of glucose concentration values corresponds to an ongoing glycemic response to a meal.

19. The method of claim 18, further comprising causing delivery of insulin to at least partially counteract the ongoing glycemic response to the meal.

20. One or more processor-readable media storing instructions which, when executed by one or more processors, cause performance of:
obtaining a plurality of glucose concentration values and a plurality of plasma insulin concentration estimations, each glucose concentration value corresponding in time with a respective plasma insulin concentration estimation to form a plurality of time-corresponding pairs of glucose concentration values and plasma insulin concentration estimations;
generating an output based on applying a meal detection model to the plurality of glucose concentration values and the plurality of plasma insulin concentration estimations; and
determining, based on the output, that a glucose concentration value of the plurality of glucose concentration values corresponds to an ongoing glycemic response to a meal.

* * * * *